(12) United States Patent
Collins et al.

(10) Patent No.: US 7,591,995 B2
(45) Date of Patent: Sep. 22, 2009

(54) COBALAMIN CONJUGATES USEFUL AS IMAGING AND THERAPEUTIC AGENTS

(75) Inventors: Douglas A. Collins, Rochester, MN (US); Henricus P. C. Hogenkamp, Roseville, MN (US)

(73) Assignees: Mayo Foundation for Medical Education and Research, Rochester, MN (US); Regents of the University of Minnesota, Saint Paul, MN (US)

( * ) Notice: Subject to any disclaimer, the term of this patent is extended or adjusted under 35 U.S.C. 154(b) by 363 days.

(21) Appl. No.: 11/555,034

(22) Filed: Oct. 31, 2006

(65) Prior Publication Data

US 2007/0116644 A1 May 24, 2007

Related U.S. Application Data

(63) Continuation-in-part of application No. 10/785,266, filed on Feb. 24, 2004, now Pat. No. 7,179,445, which is a continuation of application No. 09/690,353, filed on Oct. 16, 2000, now Pat. No. 6,838,073, which is a continuation-in-part of application No. PCT/US00/10098, filed on Apr. 15, 2000.

(60) Provisional application No. 60/159,753, filed on Oct. 15, 1999.

(51) Int. Cl.
A61K 51/00 (2006.01)
A61M 36/14 (2006.01)

(52) U.S. Cl. .................. 424/1.73; 424/1.11; 424/1.65; 424/1.69

(58) Field of Classification Search ............ 424/1.11, 424/1.65, 1.69, 9.1, 9.3, 9.4, 9.5, 9.6, 9.7, 424/181, 1.85, 1.73; 534/7, 10–16; 514/2, 514/10; 536/26.4
See application file for complete search history.

(56) References Cited

U.S. PATENT DOCUMENTS

| | | | |
|---|---|---|---|
| 3,627,788 A | 12/1971 | Bouchaudon et al. | |
| 3,936,440 A | 2/1976 | Nath | |
| 3,981,863 A | 9/1976 | Niswender et al. | |
| 4,209,614 A | 6/1980 | Bernstein et al. | |
| 4,279,859 A | 7/1981 | Gutcho et al. | |
| 4,283,342 A | 8/1981 | Yolles | |
| 4,301,140 A | 11/1981 | Frank et al. | |
| 4,465,775 A | 8/1984 | Cidlowski et al. | |
| 4,612,302 A | 9/1986 | Szabo et al. | |
| 4,672,028 A | 6/1987 | Olson | |
| 4,684,620 A | 8/1987 | Hruby et al. | |
| 4,853,371 A | 8/1989 | Coy et al. | |
| 4,959,356 A | 9/1990 | Miura et al. | |
| 4,987,071 A | 1/1991 | Cech et al. | |
| 5,057,301 A | 10/1991 | Wilbur et al. | |
| 5,187,107 A | 2/1993 | Watkins et al. | |
| 5,286,853 A | 2/1994 | Spielvogel et al. | |
| 5,308,606 A | 5/1994 | Wilson et al. | |
| 5,372,808 A | 12/1994 | Blatt et al. | |
| 5,405,598 A | 4/1995 | Schinazi et al. | |
| 5,405,839 A | 4/1995 | Toraya et al. | |
| 5,428,023 A | 6/1995 | Russell-Jones et al. | |
| 5,462,724 A | 10/1995 | Schinazi et al. | |
| 5,589,463 A | 12/1996 | Russell-Jones et al. | |
| 5,599,796 A | 2/1997 | Schinazi et al. | |
| 5,608,060 A | 3/1997 | Axworthy et al. | |
| 5,630,786 A | 5/1997 | Griffin et al. | |
| 5,736,392 A | 4/1998 | Hawley-Nelson et al. | |
| 5,739,313 A * | 4/1998 | Collins et al. ............ | 536/26.44 |
| 5,807,832 A | 9/1998 | Russell-Jones et al. | |
| 5,840,880 A | 11/1998 | Morgan, Jr. et al. | |
| 5,869,465 A | 2/1999 | Morgan, Jr. et al. | |
| 5,869,466 A | 2/1999 | Russell-Jones et al. | |
| 5,872,107 A | 2/1999 | Schinazi et al. | |
| 5,877,165 A | 3/1999 | Miura et al. | |
| 5,879,465 A | 3/1999 | McKevitt et al. | |
| 5,936,082 A | 8/1999 | Bauer | |
| 6,004,533 A | 12/1999 | Collins et al. | |
| 6,017,902 A | 1/2000 | Glass et al. | |
| 6,056,973 A | 5/2000 | Allen et al. | |
| 6,071,545 A | 6/2000 | Hendler et al. | |
| 6,074,625 A | 6/2000 | Hawthorne et al. | |
| 6,083,926 A | 7/2000 | Morgan, Jr. et al. | |
| 6,093,701 A | 7/2000 | Wolff et al. | |
| 6,096,290 A | 8/2000 | Collins et al. | |
| 6,107,902 A | 8/2000 | Zhang et al. | |
| 6,150,341 A | 11/2000 | Russell-Jones et al. | |
| 6,153,737 A | 11/2000 | Manoharan et al. | |
| 6,159,502 A | 12/2000 | Russell-Jones et al. | |
| 6,159,734 A | 12/2000 | McKay et al. | |
| 6,165,720 A | 12/2000 | Felgner et al. | |
| 6,165,789 A | 12/2000 | Monia et al. | |
| 6,180,766 B1 | 1/2001 | Schinazi et al. | |
| 6,183,723 B1 | 2/2001 | Seetharam et al. | |
| 6,211,355 B1 * | 4/2001 | Collins et al. ............ | 536/26.41 |
| 6,214,535 B1 | 4/2001 | Matsumori | |
| 6,221,397 B1 | 4/2001 | Russell-Jones et al. | |

(Continued)

FOREIGN PATENT DOCUMENTS

DE 1 811 518 7/1969

(Continued)

OTHER PUBLICATIONS

U.S. Appl. No. 09/690,198, filed Oct. 16, 2000.

(Continued)

*Primary Examiner*—D L Jones
(74) *Attorney, Agent, or Firm*—Fish & Richardson P.C.

(57) ABSTRACT

The invention provides detectably labeled cobalamin derivatives which are useful for medical treatment and diagnosis.

38 Claims, 5 Drawing Sheets

U.S. PATENT DOCUMENTS

| | | | |
|---|---|---|---|
| 6,262,253 | B1 | 7/2001 | Russell-Jones et al. |
| 6,274,564 | B1 | 8/2001 | Sarill et al. |
| 6,291,184 | B1 | 9/2001 | Gold et al. |
| 6,315,978 | B1 | 11/2001 | Grissom et al. |
| 6,395,492 | B1 | 5/2002 | Manoharan et al. |
| 6,613,305 | B1* | 9/2003 | Collins et al. ............... 424/1.73 |
| 6,777,237 | B2 | 8/2004 | Grissom |
| 6,806,363 | B1* | 10/2004 | Collins et al. ............... 536/26.4 |
| 6,838,073 | B1* | 1/2005 | Collins et al. ............... 424/1.69 |
| 6,962,906 | B2 | 11/2005 | Efimov et al. |
| 7,141,233 | B2* | 11/2006 | Collins et al. ................ 424/9.1 |
| 7,179,445 | B2* | 2/2007 | Collins et al. ............... 424/1.69 |
| 7,462,345 | B2 | 12/2008 | Collins et al. |
| 7,468,432 | B2 | 12/2008 | Collins et al. |
| 2002/0002146 | A1 | 1/2002 | Halevie-Goldman |
| 2002/0042394 | A1 | 4/2002 | Hogenkamp et al. |
| 2002/0049155 | A1 | 4/2002 | Hogenkamp |
| 2002/0151525 | A1 | 10/2002 | Collins et al. |
| 2003/0018009 | A1 | 1/2003 | Collins |
| 2003/0144198 | A1 | 7/2003 | Collins |
| 2004/0162240 | A1 | 8/2004 | Collins et al. |
| 2005/0004010 | A1 | 1/2005 | Collins et al. |

FOREIGN PATENT DOCUMENTS

| | | |
|---|---|---|
| EP | 0 005 834 | 10/1981 |
| EP | 0 069 450 | 4/1985 |
| EP | 0 165 716 | 1/1990 |
| EP | 0 220 030 | 6/1991 |
| EP | 2 088 364 | 8/1996 |
| EP | 0 506 242 | 12/1998 |
| JP | 58-46027 | 3/1983 |
| WO | WO 89/01475 | 2/1989 |
| WO | WO 92/09610 | 6/1992 |
| WO | WO 92/13571 | 8/1992 |
| WO | WO 94/27613 | 12/1994 |
| WO | WO 94/27641 | 12/1994 |
| WO | WO 95/27723 | 10/1995 |
| WO | WO 96/04016 | 2/1996 |
| WO | WO 96/27641 | 9/1996 |
| WO | WO 96/31243 | 10/1996 |
| WO | WO 97/14711 | 4/1997 |
| WO | WO 97/18231 | 5/1997 |
| WO | WO 97/33627 | 9/1997 |
| WO | WO 98/08859 | 3/1998 |
| WO | WO 99/29302 | 6/1999 |
| WO | WO 99/65529 | 12/1999 |
| WO | WO 99/65930 | 12/1999 |
| WO | WO 00/25793 | 5/2000 |
| WO | WO 00/45857 | 8/2000 |
| WO | WO 00/62808 | 10/2000 |
| WO | WO 00/74721 | 12/2000 |
| WO | WO 01/00646 | 1/2001 |
| WO | WO 01/17694 | 3/2001 |
| WO | WO 01/28592 | 4/2001 |
| WO | WO 01/28595 | 4/2001 |
| WO | WO 01/30967 | 5/2001 |
| WO | WO 01/53311 | 7/2001 |
| WO | WO 01/92283 | 12/2001 |
| WO | WO 01/92288 | 12/2001 |
| WO | WO 02/42318 | 5/2002 |
| WO | WO 02/55530 | 7/2002 |
| WO | WO 03/00010 | 1/2003 |
| WO | WO 03/25139 | 3/2003 |

OTHER PUBLICATIONS

U.S. Appl. No. 10/028,875, filed Oct. 22, 2001.
U.S. Appl. No. 60/129,733, filed Apr. 16, 1999.
U.S. Appl. No. 60/159,753, filed Oct. 15, 1999.
U.S. Appl. No. 60/159,873, filed Oct. 15, 1999.
U.S. Appl. No. 60/159,874, filed Oct. 15, 1999.

Akine et al., "Neutron-capture therapy of murine ascites tumor with gadolinium-containing microcapsules," *J. Cancer Res. Clin. Oncol.*, 1992, 119:71-73.

Allen, "Human Vitamin $B_{12}$ Transport Proteins," *Progress in Hematology*, 1975, 9:57-84.

Alvarez et al., "On a New Radiopharmaceutical for Kidney Imaging," *Intl. J. Appl. Radiation and Isotopes*, 1974, 25(6):283-284.

Amagasaki et al., "Expression of Transcobalamin II-Receptors by Human Leukemia K562 and HL- 60 Cells," *Blood*, 1990, 76(7):1380-1386.

Anton et al., "Carbon-13 Nuclear Magnetic Resonance Studies of the Monocarboxylic Acids of Cyanocobalamin. Assignments of the b-, d-, and e-Monocarboxylic Acids," *J. Am. Chem. Soc.*, 1980, 102(7):2215-2219.

Anton et al., "The Synthesis and Properties of Four Spin-labeled Analogs of Adenosylcobalamin," *J. Biol. Chem.*, 1980, 255(10):4507-4510.

Armitage et al., "Chemistry of the Vitamin $B_{12}$ Group. Part III. The Course of Hydrolytic Degradations," *J. Chem. Soc.*, 1953, 3849-3864.

Begley et al., "Cobalamin Metabolism in Cultured Human Chorionic Villus Cells," *J. Cell. Physiol.*, 1993, 156:43-47.

Bernhauer et al., "Zur Chemie and Biochemie der Corrinoide," *Biochem. Z*, 1966, 344:289-309.

Blomquist et al., "Uptake of Labelled Vitamin $B_{12}$ and 4-Iodophenylalanine in some Tumours of Mice," *Experientia*, 1969, 25:294-296.

Breeman et al., "Indium-111 labeled DTPA- and DOTA-bombesin analogs for receptor scintigraphy and radiotherapy," *Proc. of the 46t Annual Meeting of the Society of Nuclear Medicine*, Los Angeles, California, Jun. 6-10, 1999, *J. Nuc. Med.*, 40(5):102P, Abstract No. 418 (May 1999 supplement).

Cannon et al., "Synthesis and Uptake of a Radiolabeled Cobalamin Bioconjugate," *9th International Symposium on Recent Advances in Drug Delivery Systems*, Feb. 1999, pp. 230-231.

Chaiet et al., "Biosynthesis of Radioactive Vitamin $B_{12}$ Containing Cobalt$^{60}$," *Science*, 1950, 111:601-602.

Collins et al., "Biodistribution of Radiolabeled Adenosylcobalamin in Patients Diagnosed With Various Malignancies," *Mayo Clin Proc.*, 2000, 75:568-580.

Collins et al., "Tumor Imaging Via Indium 111-Labeled DTPA-Adensylcobalamin," *Mayo Clin Proc.*, 1999, 74:687-691.

Cooper and Paranchych, "Selective Uptake of Specifically Bound Cobalt-58 Vitamin $B_{12}$ by Human and Mouse Tumour Cells" *Nature*, 1961, 191:393-395.

Cooperman, "Distribution of Radioactive and Nonradioactive Vitamin $B_{12}$ in Normal and Malignant Tissues of an Infant with Neuroblastoma," *Cancer Research*, 1972, 32:167-172.

Cooperman et al., "Distribution of Radioactive and Nonradioactive Vitamin $B_{12}$ in the Dog," *J. Biol. Chem.*, 1960, 235:191-194.

CTEP [Developing Cancer Therapies], "FDA Approved Anti-Cancer Drugs" (Jan. 1, 1997), at http://ctep.info.nih.gov/handbook/HandBookTex/fda_agen.htm, accessed Nov. 14, 2000.

de Jong et al., "Radionuclide therapy using radiolabeled somatostatin analogs in tumors-bearing rats," *Proc. of the 46th Annual Meeting of the Society of Nuclear Medicine*, Los Angeles, California, Jun. 6-10, 1999, *J. Nuc. Med.*, 40(5):102, Abstract No. 414 (May 1999 supplement).

Ellenbogen, "Absorption and transport of cobalamin: Intrinsic factor and the transcobalamins," *Cobalamin: Biochemistry and Pathophysiology*, 1975, Chapter 5, Babior (ed.), John Wiley & Sons, New York.

Fedosov et al., "Binding of Cobalamin and Cobinamide to Transcobalamin from Bovine Milk," *Biochemistry*, 1995, 34:16082-16087.

Fedosov et al., "Transcobalamin from cow milk: isolation and physico-chemical properties," *Biochem. Biophys. Acta*, 1996, 1292:113-119.

Finkler and Hall, "Nature of the Relationship between Vitamin $B_{12}$ Binding and Cell Uptake," *Arch. Biochem. Biophys.*, 1967, 120:79-85.

Flodh, "Accumulation of Labelled Vitamin $B_{12}$ in Some Transplanted Tumours," *Distribution and Kinetics of Labeled Vitamin B12, Acta Radiologica*, 1968, Supplementum 284, pp. 55-60.

Flodh and Ullberg, "Accumulation of Labelled Vitamin $B_{12}$ in Some Transplanted Tumours," *Int. J. Cancer*, 1968, 3:694-699.

Gennaro, *Remington: The Science and Practice of Pharmacy*, 1995, 19th Ed., vol. 2, Mack Publishing Co., pp. 1527-1529, 1561.

Gottlieb et al., "Rapid Charcoal Assay for Intrinsic Factor (IF), Gastric Juice Unsaturated B 12 Binding Capacity, Antibody to IF, and Serum Unsaturated B12 Binding Capacity," *Blood*, 1965, 25(6):875-884.

Grossowicz et al., "Isotopic Determination of Vitamin $B_{12}$ Binding Capacity and Concentration," Proc. Exp. Biol., 1962, 109:604-608.

Guy et al., "Evaluation of coupling of cobalamin to antisense oligonucleotides by thin-layer and reversed-phase liquid chromatography," *J. Chromatog. B*, 1998, 709:149-156.

Hall et al., "Cyclic Activity of the Receptors of Cobalamin Bound to Transcobalamin II," *J. Cell. Physiol.*,1987, 133:187-191.

Hatanaka, "A revised boron-neutron capture therapy for malignant brain tumors," *Journal of Neurology*, 1975, 209:81-94.

Higashi et al., "In Vitro Assessment of 2-Fluoro-2-Deoxy-D-Glucose, L-Methionine and Thymidine as Agents to Monitor the Early Response of a Human Adenocarcinoma Cell Line to Radiotherapy," *J. Nucl. Med.*, 1993, 34:773-779.

Hogenkamp, Chemical Synthesis and Properties of Analogs of Adenosylcobalamin, *Biochemistry*, 1974, 13(13):2736-2739.

Hogenkamp et al., "Carbon-13 Nuclear Magnetic Resonance Studies of Adenosylcobalamin and Alkylcorrinoids, Selectively Enriched with Carbon-13," *Biochemistry*, 1975, 14(16):3707-3714.

Hogenkamp et al., "Diagnostic and Therapeutic Analogues of Cobalamin," *Chemistry and Biochemistry of $B_{12}$*, Part II, Banerjee (ed.), Wiley & Sons, Section 15:385-410.

Hogenkamp et al., "Synthesis and Characterization of *nido*-Carborane-Cobalamin Conjugates," *Nucl. Med. & Biol.*, 2000, 27:89-92.

Kahl and Micca, "Chemical and biological studies on boronated tetraphenyl porphyrins," *Boron Neutron Capture Therapy for Tumors*, 1986, Hatanaka (ed.), Niigata, Japan: Nishimura Co., Ltd., pp. 61-67.

Kaplan et al., "Absorptions Studies of $^{59}$Fe and $^{58}$Co Vitamin $B_{12}$ by Whole-Body Radiometry in the Radiation Therapy of Collum Carcinoma," *Radiobiol. Radiother.*, 1983, 24:745-752, English Abstract included.

Kubota et al., "Tracer Feasibility for Monitoring Tumor Radiotherapy: A Quadruple Tracer Study with Fluorine-18-Fluorodeoxyglucose or Fluorine-18-Fluorodeoxyuridine, L-[Methyl-$^{14}$C]Methionine, [6-$^{3}$H]Thymidine, and Gallium-67," *J. Nucl. Med.*, 1991 32(11):2118-2123.

Lindemans et al., "Uptake of Transcobalamin II-Bound Cobalamin by HL-60 Cells: Effects of Differentiation Induction," *Experimental Cell Research*, 1989, 184(2):449-460.

Louisiana State University Cancer Treatment Center, "Chemotherapeutic Agents Commonly used in Veterinary Medicine", http://www.vetmed.lsu.edu/oncology/Chemotherapy.htm, accessed Nov. 14, 2000.

Luo et al., "Studies on bone tumor therapeutic radiopharmaceuticals IV, Investigation of the structure-activity-relationships (SARS) of $^{153}$Sm-aminocarboxylate complexes," *Proc. of the 46th Annual Meeting of the Society of Nuclear Medicine*, Los Angeles, California, Jun. 6-10, 1999, *J. Nuc. Med.*, 40(5):316P, Abstract No. 1386 (May 1999 supplement).

Masiakowski et al., "Gadolinium neutron capture therapy for brain tumors: A computer study," *Med. Phys.*, 1992, 19(5):1277-1284.

McBride, "A general method for the introduction of metal binding ligands onto the side chains of peptides during peptide synthesis," *Proc. of the 46th Annual Meeting of the Society of Nuclear Medicine*, Los Angeles, California, Jun. 6-10, 1999, *J. Nuc. Med.*, 40(5):124P, Abstract No. 500 (May 1999 supplement).

McLean et al., "Antibodies to Transcobalamin II Block in Vitro Proliferation of Leukemic Cells," *Blood*, 1997, 89(1):235-242.

Mease et al., "Indium-11 1 CDTA-(aminostyryl)pyridiniumum (diX-asp) dyes: synthesis, canine and human leukocyte labeling, and serum stability," *Proc. of the 46' Annual Meeting of the Society of Nuclear Medicine*, Los Angeles, California, Jun. 6-10, 1999, *J. Nuc. Med.*, 40(5):318P, Abstract No. 1396 (May 1999 supplement).

Momen et al., "Impact of high resolution bone spect imaging of the thoracolumbar spine on patient management in oncology," *Proc. of the 46th Annual Meeting of the Society of Nuclear Medicine*, Los Angeles, California, Jun. 6-10, 1999, *J. Nuc. Med.*, 40(5):102P, Abstract No. 413 (May 1999 supplement).

Knudsen and Nielsen, "Application of peptide nucleic acid in cancer therapy," *Anti-Cancer Drugs*, 1997, 8:113-118.

Nielsen et al., "Sequence-Selective Recognition of DNA by Strand Displacement with a Thymine- Substituted Polyamide," *Science*, 1991, 254:1497-1500.

Norenberg, "[213Bi-DOTA°,Tyr']octreotide (213Bi-DOTATOC) in peptide receptor radionuclide therapy (PRRT)," *Proc. of the 46th Annual Meeting of the Society of Nuclear Medicine*, Los Angeles, California, Jun. 6-10, 1999, *J. Nuc. Med.*, 40(5):103, Abstract No. 415 (May 1999 supplement).

Order et al., "Use of Isotopic Immunoglobulin in Therapy," *Cancer Res.*, 1980, 40:3001-3007.

Pathare et al., "Synthesis of Cobalamin-Biotin Conjugates That Vary in the Position of Cobalamin Coupling. Evaluation of Cobalamin Derivative Binding to Transcobalamin II," *Bioconj. Chem.*, 1996, 7(2):217-232.

Ruiz et al., "Influence of average molecular weights of poly(DL-lactic acid-co-glycolic acid) copolymers 50/50 on phase separation and in vitro drug release from microspheres," *Pharmaceutical Research*, 1990, 7(9):928-934.

Pinson et al., "Synthesis of Two Doxorubicin-Cobalamin Bioconjugates," *9th International Symposium on Recent Advances in Drug Delivery Systems*, Feb. 1999, pp. 228-229.

Pinson et al., "Synthesis, protein binding, and cellular uptake of doxorubicin—cobalamin bioconjugates," 219th Meeting of the American Chemical Society, San Francisco, California, Mar. 26-30, 2000 (Abstracts of Papers of the American Chemical Society, (2000) vol. 219, No. 1-2, Abstract.

Ponto, "II. Schilling Test," *Pharmaceuticals in Medical Imaging*, 1990, Swanson et al., (eds.), Macmillan Publishing Co., Inc., New York, pp. 621-628.

Primus, "Bispecific antibody mediated targeting of nido-carboranes to human colon carcinoma cells," *Bioconjugate Chemistry*, 1996, 7:532-535.

Purdue University School of Veterinary Medicine,"Chemotherapy Drugs to Know," MCMP 611, Spring 1997, http://www.vet.purdue.edu/bms/courses/mcmp611/chmrx/drg2no61.htm, accessed Nov. 14, 2000.

Rao et al., "TC-99M labeled peptide for imaging infection," *Proc. of the 46th Annual Meeting of the Society of Nuclear Medicine*, Los Angeles, California, Jun. 6-10, 1999), *J. Nuc. Med.*, 40(5):319P, Abstract No. 1398 (May supplement).

Rappazzo and Hall, "Transport Function of Transcobalamin II," *J. Clin. Invest.*, 1972, 51:1915-1918.

Roe et al., "Combinatorially designed technetium radiopharmaceuticals (CDTR'M)," *Proc. of the 46th Annual Meeting of the Society of Nuclear Medicine*, Los Angeles, California, Jun. 6-10, 1999, *J. Nuc. Med.*, 40(5):123P, Abstract No. 499 (May 1999 supplement).

Russell-Jones et al., "Vitamin $B_{12}$ Mediated Oral Delivery Systems for Granulocyte-Colony Stimulating Factor and Erythropoietin," *Bioconjugate Chem.*, 1995, 6(4):459-465.

Sattelberger and Atcher, "Nuclear medicine finds the right chemistry," *Nature Biotechnology*, 1999, 17:849-850.

Shih and Brugger, "Gadolinium as a neutron capture therapy agent," *Med. Phys.*, 1992, 19:733-744.

Smeltzer et al., "Cytotoxicities of Two Cobalamin Bioconjugates," 9th International Symposium on Recent Advances in Drug Delivery Systems, Feb. 1999, pp. 232-233.

Smeltzer et al., "Synthesis and Characterization of Fluorescent Cobalamin (CobalaFluor) Derivatives for Imaging," *Organic Letters*, 2001, 3(6):799-801.

Soda et al., "Receptor Distribution and the Endothelial Uptake of Transcobalamin II in Liver Cell Suspensions," *Blood*, 1985, 65(4):795-802.

Svanvik et al., "Light-Up Probes: Thiazole Orange-Conjugated Peptide Nucleic Acid for Detection of Target Nucleic Acid in Homogeneous Solution," *Analytical Biochemistry*, 2000, 281:26-35.

Takakura and Hashida, "Macromolecular drug carrier systems in cancer chemotherapy: macromolecular prodrugs," *Crit. Rev. Oncology: Hematology*, 1995, 18:207-231.

The Merck Index an Encyclopedia of Chemicals, Drugs, and Biologicals, 1989, Eleventh Edition Budavari et al. (eds.), p. 1577.

The Merck Index an Encyclopedia of Chemicals, Drugs, and Biologicals, 1996, Twelfth Edition Budavari et al. (eds.), p. 1710.

Uchino et al., "Tissue Distribution of Coenzyme $B_{12}$ in Rats Following Intravenous Administration," *Ann. N. Y. Acad. Sci.*, 1964, 112(Art. 2):844-854.

van Eijkeren et al., "Measurement of short-term 11C-thymidine activity in human head and neck tumours using positron emission tomography (PET)," *Acta Oncol.*, 1992, 31(5):539-543.

Vares and Myasishcheva, "Kinetic of $^{57}$Co-Cyanocobalamin Distribution in Organs and Tissues of Mice with Transplanted Tumours," *Eksp. Onkol.*, 1986, 8:33-36, English Abstract.

Walker et al., "The Chemical Synthesis and Nuclear Magnetic Resonance Spectroscopy of Adenosylcobalamin Selectively Enriched with Carbon-13," *Biochemistry*, 1974, 13(12):2650-2655.

Wierzbicici et al., "Measurement of augmentation of $^{252}$Cf implant by $^{10}$B and $^{157}$Gd neutron capture," *Med. Phys.*, 1994, 21(6):787-790.

Wilbur et al., "Biotin Reagents for Antibody Pretargeting. 4. Selection of Biotin Conjugates for in Vivo Application Based on Their Dissociation Rate from Avidin and Streptavidin," *Bioconjugate Chem.*, 2000, 11(4):569-583.

Wilbur et al., "Evaluation of Biotin-Dye Conjugate for Use in an HPLC Assay to Assess Relative Binding of Biotin Derivatives with Avidin and Streptavidin," *Bioconjugate Chem.*, 2000, 11(4):584-598.

Woolley et al., "Uptake of [C0-57]-Vitamin B-12 by Murine Tumours of Many Histologic Types," Clinical Research, 1993, Abstracts of National Meeting, Association of American Physicians, p. 73A.

Wu et al., "Investigations of N-linked Macrocycles for $^{111}$In and $^{90}$Y Labeling of Proteins," *Nucl. Med. Biol.*, 1992, 19(2):239-244.

Yamada and Hogenkamp, "The Synthesis of a 5'-Deoxyadenosylcobalamin-agarose Adsorbent and Its Utility in the Purification of Ribonucleotide Reductase," *J. Biol. Chem.*, 1972, 247(19):6266-6270.

Yong et al., "In Vitro and in Vivo Evaluation of *o*-Carboranylalanine as a Potential Boron Delivery Agent for Neutron Capture Therapy," *Anticancer Research*, 1995, 15:2033-2038.

"Current Status of Neutron Capture Therapy" International Atomic Energy Agency, May 2001, pp. 1-292.

Anderson et al., "Preparation, Biodistribution and Dosimetry of Copper-64-Labeled Anti-Colorectal Carcinoma Monoclonal Antibody Fragments 1A3-F (ab')$_2$," *J. Nucl. Med.*, 1995, 36:850-858.

Broan et al., "Synthesis and Complexation Behaviour of an Effective Octadentate Complexone 1,4,7,10-Tetraazacyclododecane-1,4,7,10-tetrakis[methylene(methylphosphinic acid)]," *J. Chem. Soc., Chem. Commun.*, 1990, 23:1739-1741.

Collins et al., "Transcobalamin II Receptor Imaging via Radiolabeled Diethylene—Triaminepentaacetate Cobalamin analogs," *J. Nucl. Med.*, 1997, 38(5):717-723.

Dolphin, "Preparation of the reduced forms of Vitamin $B_{12}$ and of some analogs of the vitamin $B_{12}$ coenzyme containing a cobalt-carbon bond," *Meth. Enzymol.*, 1971, 18:34-52.

Good and Nielsen, "Antisense inhibition of gene expression in bacteria by PNA targeted to mRNA," *Nat. Biotechnol.*, 1998, 16:355-358.

Kollmer et al., "On a new radiopharmaceutical for kidney imaging," *Int. J. Appl. Radiation Isotopes*, 1974, 25(6):283-285.

Larrea et al., "Tumor necrosis factor alpha gene expression and the response to interferon in chronic hepatitis C," *Hepatology*, 1996, 23:210-217.

U. S. Appl. No. 10/028,857, filed Oct. 25, 2001.

Morita et al., "2"-O,4"-C-ethylene-bridged nucleic acids (ENA): highly nuclease-resistant and thermodynamically stable oligonucleotides for antisense drug," *Bioorg. Med. Chem. Lett.*, 2002, 12:73-76.

Pisal et al., "Pluronic gels for delivery of Vitamin $B_{12}$. Part I: Preformulation study," *Int. J. Pharm.*, 2004, 270:37-45.

Wahlestedt et al., "Potent and nontoxic antisense oligonucleotides containing locked nucleic acids," *Proc. Natl. Acad. Sci, USA*, 2000, 97(10):5633-5638.

Wunderbaldinger et al., "New approaches for imaging in gene therapy," *Eur. J. Radiol.*, 2000, 34(3):156-165.

U.S. Appl. No. 10/028,857, filed Oct. 25, 2001.
U.S. Appl. No. 10/859,865, filed Jun. 3, 2004.
U.S. Appl. No. 10/918,638, filed Aug. 12, 2004.
U.S. Appl. No. 11/069,796, filed Feb. 28, 2005.
U.S. Appl. No. 11/353,810, filed Feb. 13, 2006.
U.S. Appl. No. 11/384,633, filed Feb. 20, 2006.
U.S. Appl. No. 10/176,138, filed Jun. 20, 2002.
U.S. Appl. No. 10/246,300, filed Sep. 17, 2002.
U.S. Appl. No. 10/262,318, filed Sep. 30, 2002.
U.S. Appl. No. 10/027,593, filed Oct. 25, 2001.
U.S. Appl. No. 12/266,763, filed Nov. 7, 2008.
U.S. Appl. No. 12/264,738, filed Nov. 4, 2008.

* cited by examiner

Synthesis of adenosyltrifluoroethylamidocobalamins

CNCbl COOH (b, d, and e)

(1, 2, and 3)

(4, 5, and 6)

(8 and 9)

Synthesis of adenosyltrifluoromethylamidocobalamin

CNCbl di COOH

| WSC
| Hydroxybenzotriazole
↓ F$_3$CCH$_2$N$^+$H$_3$Cl$^-$ (7)

Synthesis of cyano-b-trifluoroacetamidobutylamidocobalamin

| WSC
| Hydroxybenzotriazole
↓ F$_3$CCOO$^-$Na$^+$ (10)

COBALAMIN CONJUGATES USEFUL AS IMAGING AND THERAPEUTIC AGENTS

CROSS-REFERENCE TO RELATED APPLICATIONS

This application is a continuation-in-part of U.S. application Ser. No. 10/785,266 filed Feb. 24, 2004, which is a continuation of U.S. application Ser. No. 09/690,353 filed Oct. 16, 2000, now issued as U.S. Pat. No. 6,838,073, which is a continuation-in-part of International Application No. PCT/US00/10098 filed Apr. 15, 2000, which claims the benefit of U.S. Provisional Application Ser. No. 60/159,753, filed 15 Oct. 1999, each of which is incorporated herein in its entirety by reference.

TECHNICAL FIELD

The invention provides detectably labeled cobalamin derivatives which are useful for medical treatment and diagnosis.

BACKGROUND

For several years after the isolation of vitamin $B_{12}$ as cyanocobalamin in 1948, it was assumed that cyanocobalamin and possibly hydroxocobalamin, its photolytic breakdown product, occurred in man. Since then it has been recognized that cyanocobalamin is an artifact of the isolation of vitamin $B_{12}$ and that hydroxocobalamin and the two coenzyme forms, methylcobalamin and adenosylcobalamin, are the naturally occurring forms of the vitamin.

The structure of these various forms is shown in FIG. 1, wherein X is CN, OH, $CH_3$ or adenosyl, respectively. Hereinafter, the term cobalamin will be used to refer to all of the molecule except the X group. The fundamental ring system without cobalt (Co) or side chains is called corrin and the octadehydrocorrin is called corrole. FIG. 1 is adapted from *The Merck Index*, Merck & Co. (11th ed. 1989), wherein X is above the plane defined by the corrin ring and nucleotide is below the plane of the ring. The corrin ring has attached six amidoalkyl ($H_2NC(O)Alk$) substituents, at the 2, 3, 7, 8, 13, and 18 positions, which can be designated a-e and g, respectively. See D. L. Anton et al., *J. Amer. Chem. Soc.*, 102, 2215 (1980). The 2, 3, 7, 8, and 13 positions are shown in FIG. 1 as positions a-e, respectively.

Cells undergoing rapid proliferation have been shown to have increased uptake of thymidine and methionine. (See, for example, M. E. van Eijkeren et al., *Acta Oncologica*, 31, 539 (1992); K. Kobota et al., *J. Nucl. Med.*, 32, 2118 (1991) and K. Higashi et al., *J. Nucl. Med.*, 34, 773 (1993)). Since methylcobalamin is directly involved with methionine synthesis and indirectly involved in the synthesis of thymidylate and DNA, it is not surprising that methylcobalamin as well as Cobalt-57-cyanocobalamin have also been shown to have increased uptake in rapidly dividing tissue (for example, see, B. A. Cooper et al., *Nature*, 191, 393 (1961); H. Flodh, *Acta Radiol. Supnl.*, 284, 55 (1968); L. Bloomquist et al., *Experientia*, 25, 294 (1969)). Additionally, up-regulation in the number of transcobalamin II receptors has been demonstrated in several malignant cell lines during their accelerated thymidine incorporation and DNA synthesis (see, J. Lindemans et al., *Exp. Cell. Res.*, 184, 449 (1989); T. Amagasaki et al., *Blood*, 26, 138 (1990) and J. A. Begly et al., *J. Cell Physiol.*, 156, 43 (1993)).

U.S. Pat. No. 5,739,313 discloses cobalamin analogs which comprise a compound of formula I, a linking group, a chelating group and a detectable radionuclide or a detectable paramagnetic ion. The compounds localize in tumor cells following administration and are useful for imaging tumors. Although the compounds are useful as tumor imaging agents, the specific compounds prepared therein comprise one detectable radionuclide or one detectable paramagnetic ion and thus have a limited detection capability. As such, there is a need for additional imaging agents. Particular agents will have a relatively high bioavailability, a relatively low toxicity or are detectable at a relatively low concentration. In addition, there is a need for additional therapeutic agents.

SUMMARY

The present invention provides a series of novel cobalamin conjugates (i.e., conjugates of a residue of vitamin $B_{12}$ and a residue of a peptide or an amino acid comprising a radionuclide) that are useful to image tumors. The cobalamin conjugates have a low toxicity and a high specificity (i.e., they localize in tumor cells in higher concentration than normal cells). In addition, certain cobalamin conjugates of the invention include multiple detectable groups, so they can be detected at low concentrations.

The present invention also provides a compound wherein a residue of a compound of formula I (FIG. 1) is linked to one or more peptide residues or amino acid residues wherein: 1) at least one of the peptide residues or the amino acid residues is linked to one or more chelating groups comprising one or more metallic radionuclides; or 2) at least one of the peptide residues or the amino acid residues comprises one or more non-metallic radionuclides; or a pharmaceutically acceptable salt thereof.

The present invention also provides a compound wherein a residue of a compound of formula I (FIG. 1) is linked to one or more non-metallic radionuclides; or a pharmaceutically acceptable salt thereof.

The present invention also provides a compound (i.e., cobalamin conjugate of the present invention) wherein a residue of a compound of formula I is linked to one or more residues of the formula $-[NHCH[(CH_2)_4NH_2\text{-}DET]CO\text{-}]_n\text{-}Q$ wherein Q is H, ($C_1$-$C_{14}$)alkyl, or a suitable carboxy protecting group (e.g. methyl, ethyl, or benzyl; and DET is a chelating group residue comprising a metallic radionuclide and wherein n is between 2 and about 20; or a pharmaceutically acceptable salt thereof The present invention also provides a compound (i.e., cobalamin conjugate of the present invention) wherein a residue of a compound of formula I (FIG. 1) is linked to one or more residues of the formula

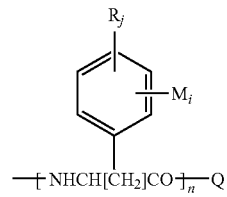

wherein each M is independently a non-metallic radionuclide; each R is independently ($C_1$-$C_{14}$)alkyl, ($C_2$-$C_{14}$)alkenyl, ($C_2$-$C_{14}$)alkynyl, ($C_1$-$C_{14}$)alkoxy, hydroxy, cyano, nitro, halo, trifluoromethyl, $N(R_a)(R_b)$, ($C_1$-$C_{14}$)alkanoyl, ($C_2$-$C_{14}$)alkanoyloxy, ($C_6$-$C_{10}$)aryl, or ($C_3$-$C_8$)cycloalkyl wherein $R_a$ and $R_b$ are each independently H or ($C_1$-$C_{14}$)alkyl; Q is H, ($C_1$-$C_{14}$)alkyl, or a suitable carboxy protecting group; n is 2 to about 20; i is 1-5, j is 0-4 and i+j is≦5; or a pharmaceutically acceptable salt thereof.

The present invention also provides a compound (i.e., cobalamin conjugate of the present invention) wherein a residue of a compound of formula I (FIG. 1) is linked to a residue of a peptide which is linked to one or more chelating groups comprising a metallic radionuclide; or a pharmaceutically acceptable salt thereof.

The present invention also provides a compound (i.e., cobalamin conjugate of the present invention) wherein a residue of a compound of formula I (FIG. 1) is linked to a residue of an amino acid which is linked to one or more chelating groups comprising a metallic radionuclide; or a pharmaceutically acceptable salt thereof.

The present invention also provides a compound (i.e., cobalamin conjugate of the present invention) wherein a residue of a compound of formula I (FIG. 1) is linked to a residue of a peptide comprising one or more non-metallic radionuclides; or a pharmaceutically acceptable salt thereof.

The present invention also provides a compound (i.e., cobalamin conjugate of the present invention) wherein a residue of a compound of formula I (FIG. 1) is linked to a residue of an amino acid comprising one or more non-metallic radionuclides; or a pharmaceutically acceptable salt thereof.

The present invention also provides a pharmaceutical composition comprising a compound of the present invention, or a pharmaceutically acceptable salt thereof, and a pharmaceutically acceptable carrier.

The present invention also provides a method of imaging a tumor in a mammal comprising administering to the mammal an effective amount of a compound of the present invention, or a pharmaceutically acceptable salt thereof, and a pharmaceutically acceptable carrier; and detecting the presence of the cobalamin conjugate.

The present invention also provides a method of treating a tumor in a mammal in need of such treatment comprising administering to the mammal an effective amount of a compound of the present invention, or a pharmaceutically acceptable salt thereof, and a pharmaceutically acceptable carrier.

The invention also provides a compound of the present invention for use in medical therapy or diagnosis.

The invention also provides the use of a compound of the present invention comprising a detectable radionuclide for the manufacture of a medicament for imaging a tumor in a mammal.

The invention also provides the use of a compound of the present invention comprising a therapeutic radionuclide for the manufacture of a medicament for treating a tumor in a mammal.

The invention also provides intermediates disclosed herein that are useful in the preparation of the compounds of the present invention as well as synthetic methods useful for preparing the compounds of the invention.

The compounds of the present invention have several characteristics which make them an attractive in vivo targeting agents. Vitamin $B_{12}$ is water soluble, has no known toxicity, and in excess is excreted by glomerular filtration. In addition, the uptake of vitamin $B_{12}$ can potentially be manipulated by the administration of nitrous oxide and other pharmacological agents (D. Swanson et al., *Pharmaceuticals in Medical Imaging*, MacMillan Pub. Co., N.Y. (1990) at pages 621-628).

The details of one or more embodiments of the invention are set forth in the accompanying drawings and the description below. Other features, objects, and advantages of the invention will be apparent from the description and drawings, and from the claims.

DETAILED DESCRIPTION

Figure 1:
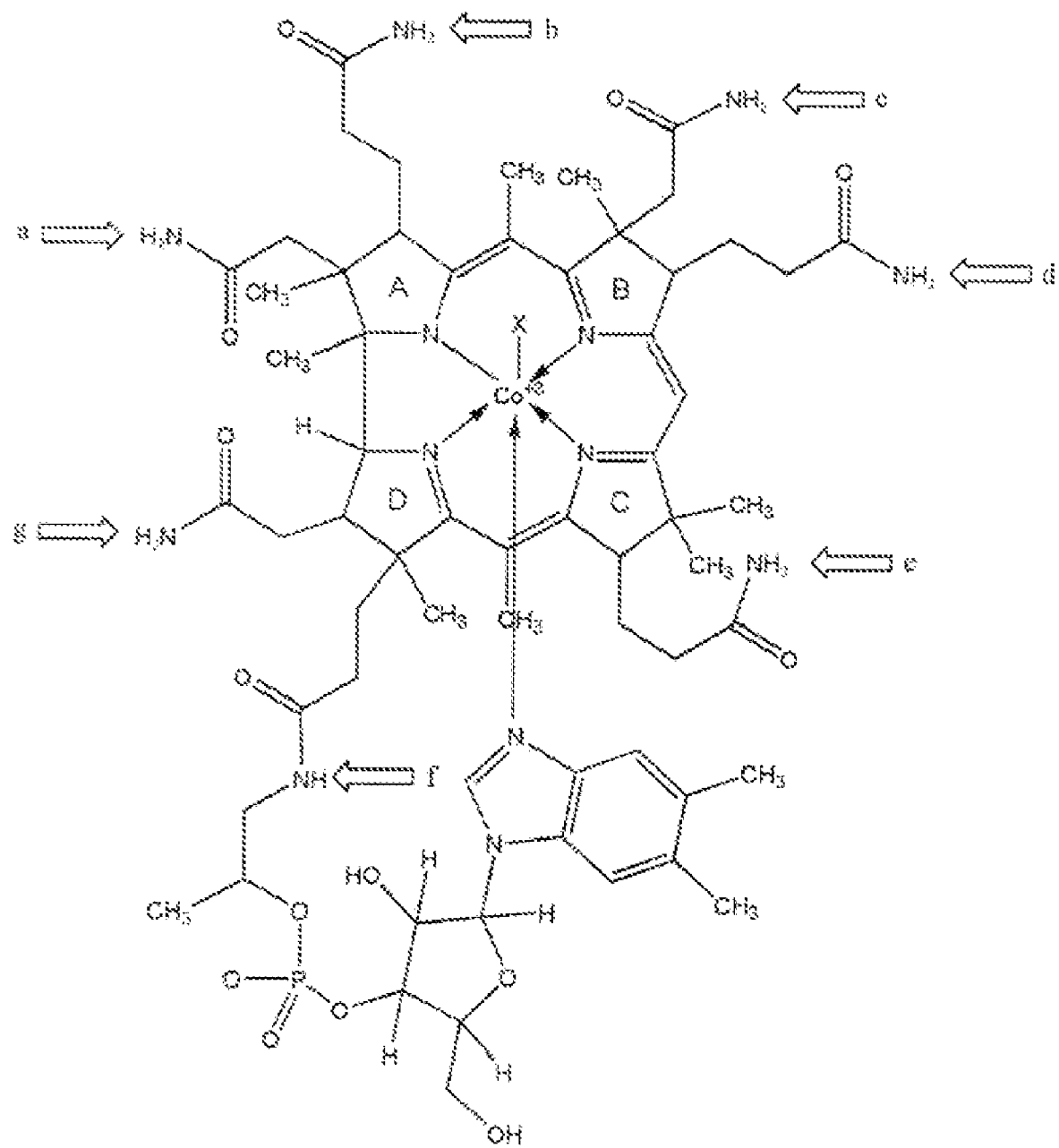
FIG. 1 illustrates a compound of formula I, wherein X is CN, OH, $CH_3$, adenosyl or a residue of a peptide or amino acid. The compound of formula I can be cyanocobalamin (X is CN), hydroxocobalamin (X is OH), methylcobalamin (X is $CH_3$), adenosylcobalamin (X is adenosyl), or a cobalamin conjugate (X is a residue of a peptide or amino acid).
Figure 2:
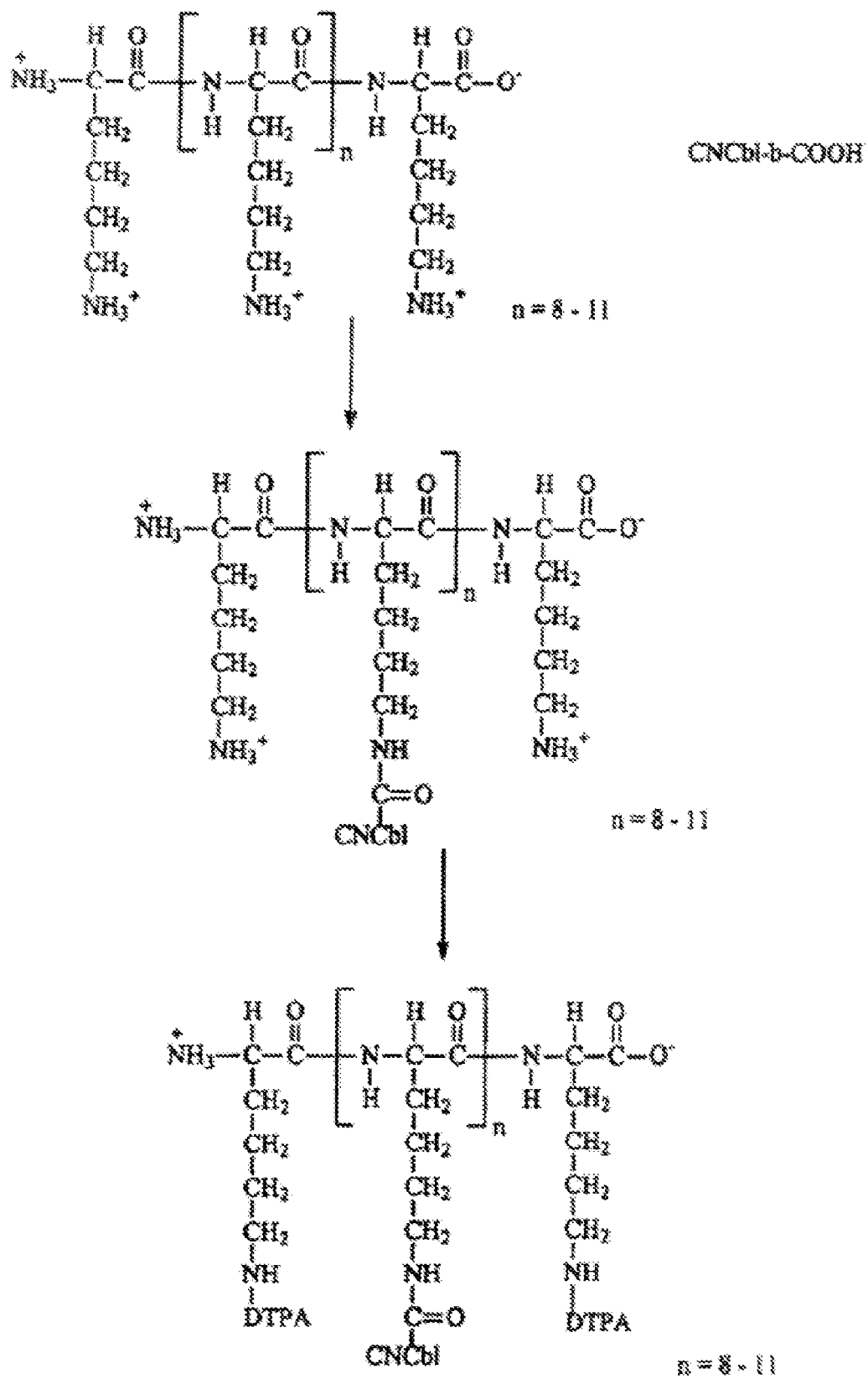
FIG. 2 illustrates a synthesis of a compound wherein a residue of a compound of formula I is linked to poly-L-lysine, 8 units to 11 units, linked to DTPA.

The following definitions are used, unless otherwise described: halo is fluoro, chloro, bromo, or iodo. Alkyl, alkoxy, alkenyl, alkyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic.

Specific and preferred values listed below for radicals, substituents, and ranges, are for illustration only; they do not exclude other defined values or other values within defined ranges for the radicals and substituents.

It is appreciated that those skilled in the art will recognize that compounds of the present invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine activity as a tumor imaging agent using the standard tests described herein, or using other similar tests which are well known in the art.

Specifically, $(C_1-C_{14})$alkyl can be methyl, ethyl, propyl, isopropyl, butyl, iso-butyl, sec-butyl, pentyl, 3-pentyl, hexyl, heptyl, octyl, nonyl, decyl undecyl, dodecyl, tridecyl or tetradecyl.

Specifically, $(C_1-C_{14})$alkoxy can be methoxy, ethoxy, propoxy, butoxy, iso-butoxy, sec-butoxy, pentoxy, 3-pentoxy, hexyloxy, heptyloxy, octyloxy, nonyloxy, decyloxy, undecyloxy, dodecyloxy, tridecyloxy, or tetradecyloxy.

Specifically, $(C_1-C_{14})$alkanoyl can be acetyl, propanoyl, butanoyl, pentanoyl, isobutanoyl, hexanoyl, heptanoyl, octanoyl, nonanoyl, decanoyl, undecanoyl, dodecanoyl, tridecanoyl, or tetradecanoyl.

Specifically, $(C_1-C_{14})$alkanoyloxy can be acetoxy, propanoyloxy, butanoyloxy, isobutanoyloxy, pentanoyloxy, hexanoyloxy, heptanoyloxy, octanoyloxy, nonanoyloxy, decanoyloxy, undecanoyloxy, dodecanoyloxy, tridecanoyloxy, or tetradecanoyloxy.

Specifically, $((C_2-C_{14})$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, 11-dodecenyl, 1-tridecenyl, 2-tridecenyl, 3-tridecenyl, 4-tridecenyl, 5-tridecenyl, 6-tridecenyl, 7-tridecenyl, 8-tridecenyl, 9-tridecenyl, 10-tridecenyl, 11-tridecenyl, 12-tridecenyl, 1-tetradecenyl, 2-tetradecenyl, 3-tetradecenyl, 4-tetradecenyl, 5-tetradecenyl, 6-tetradecenyl, 7-tetradecenyl, 8-tetradecenyl, 9-tetradecenyl, 10-tetradecenyl, 11-tetradecenyl, 12-tetradecenyl or 13-tetradecenyl.

Specifically, $(C_2-C_{14})$ alkynyl can be ethyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonylyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, 9-decynyl, 1-undecynyl, 2-undecynyl, 3-undecynyl, 4-undecynyl, 5-undecynyl, 6-undecynyl, 7-undecynyl, 8-undecynyl, 9-undecynyl, 10-undecynyl, 1-dodecynyl, 2-dodecynyl, 3-dodecynyl, 4-dodecynyl, 5-dodecynyl, 6-dodecynyl, 7-dodecynyl, 8-dodecynyl, 9-dodecynyl, 10-dodecynyl, 11-dodecynyl, 1-tridecynyl, 2-tridecynyl, 3-tridecynyl, 4-tridecynyl, 5-tridecynyl, 6-tridecynyl, 7-tridecynyl, 8-tridecynyl, 9-tridecynyl, 10-tridecynyl, 11-tridecynyl, 12-tridecynyl, 1-tetradecynyl, 2-tetradecynyl, 3-tetradecynyl, 4-tetradecynyl, 5-tetradecynyl, 6-tetradecynyl, 7-tetradecynyl, 8-tetradecynyl, 9-tetradecynyl, 10-tetradecynyl, 11-tetradecynyl, 12-tetradecynyl or 13-tetradecynyl.

Specifically, "aryl" can be phenyl, indenyl, or naphthyl.

Specifically, $(C_3-C_8)$cycloalkyl can be cyclopropyl, cyclobutyl, cyclcopentyl, cyclohexyl, cyclohepyl or cyclooctyl.

As used herein, a "residue of a compound of formula I" is a radical of a compound of formula I having one or more open valences. Any synthetically feasible atom or atoms of the compound of formula I may be removed to provide the open valence, provided bioactivity is substantially retained. Based on the linkage that is desired, one skilled in the art can select suitably functionalized starting materials that can be derived from a compound of formula I using procedures that are known in the art. For example, suitable atoms that may be removed include the $NH_2$ group of the a-carboxamide (illustrated in FIG. 1) or a hydrogen atom from the $NH_2$ group of the acarboxamide, the $NH_2$ group of the b-carboxamide (illustrated in FIG. 1) or a hydrogen atom from the $NH_2$ group of the b-carboxamide, the $NH_2$ group of the d-carboxamide (illustrated in FIG. 1) or a hydrogen atom from the $NH_2$ group of the d-carboxamide, the $NH_2$ group of the e-carboxamide (illustrated in FIG. 1) or a hydrogen atom from the $NH_2$ group of the e-carboxamide, and X at the 6-position (illustrated in FIG. 1). In addition, the hydrogen atom of the hydroxy group at the 3' position of the sugar, the hydrogen atom from the hydroxyl group at the 3' position of the sugar, the hydrogen atom of the $CH_2OH$ group at the 5' position, or the hydrogen atom from the hydroxyl group at the 5' position of the sugar ring may be removed.

As used herein, "adenosyl" is an adenosine radical in which any synthetically feasible atom or group of atoms have been removed, thereby providing an open valence. Synthetically feasible atoms which may be removed include the hydrogen atom of the hydroxy group at the 5' position. Accordingly, adenosyl can conveniently be attached to the 6-position of a compound of-formula I via the 5' position of adenosyl.

As used herein, an "amino acid" is a natural amino acid residue (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acid (e.g. phosphoserine; phosphothreonine; phosphotyrosine; hydroxyproline; gamma-carboxyglutamate; hippuric acid; octahydroindole-2-carboxylic acid; statine; 1,2,3,4,-tetrahydroisoquinoline-3-carboxylic acid; penicillamine; ornithine; citruline; α-methyl-alanine; para-benzoylphenylalanine; phenylglycine; propargylglycine; sarcosine; and tert-butylglycine) residue having one or more open valences. The term also comprises natural and unnatural amino acids bearing amino protecting groups (e.g. acetyl, acyl, trifluoroacetyl, or benzyloxycarbonyl), as well as natural and unnatural amino acids protected at carboxy with protecting groups (e.g. as a $(C_1-C_6)$alkyl, phenyl or benzyl ester or amide). Other suitable amino and carboxy protecting groups are known to those skilled in the art (See for example, T. W. Greene, *Protecting Groups In Organic Synthesis*; Wiley: New York, 1981; D. Voet, *Biochemistry*, Wiley: New York, 1990; L. Stryer, *Biochemistry*, (3rd Ed.), W. H. Freeman and Co.: New York, 1975; J. March, *Advanced Organic Chemistry, Reactions, Mechanisms and Structure*, (2nd Ed.), McGraw Hill: New York, 1977; F. Carey and R. Sundberg, *Advanced Organic Chemistry Part B: Reactions and Synthesis*, (2nd Ed.), Plenum: New York, 1977; and references cited therein). According to the invention, the amino or carboxy protecting group can also comprise a radionuclide (e.g., Fluorine-18, Iodine-123, or Iodine-124).

Specifically, when the residue of a compound of formula I is linked to a single amino acid residue linked to a chelating group comprising a metallic radionuclide, the amino acid does not have the formula $H_2N-(CH_2)_5COOH$.

As used herein, a "peptide" is a sequence of 2 to 25 amino acids (e.g. as defined hereinabove) or peptidic residues having one or more open valences. The sequence may be linear or cyclic. For example, a cyclic peptide can be prepared or may result from the formation of disulfide bridges between two cysteine residues in a sequence. A peptide can be linked through the carboxy terminus, the amino terminus, or through any other convenient point of attachment, such as, for example, through the sulfur of a cysteine. Peptide derivatives can be prepared as disclosed in U.S. Pat. Nos. 4,612,302; 4,853,371; and 4,684,620, or as described in the Examples hereinbelow. Peptide sequences specifically recited herein are written with the amino terminus on the left and the carboxy terminus on the right.

Specifically, the peptide can be poly-L-lysine, poly-L-glutamic acid, poly-L-aspartic acid, poly-L-histidine, poly-L-ornithine, poly-L-serine, poly-L-threonine, poly-L-tyrosine, poly-L-lysine-L-phenylalanine or poly-L-lysine-L-tyrosine.

The peptide residue or amino acid residue can conveniently be linked to the residue of a compound of formula I through an amide (e.g. —N(R)C(=O)— or —C(=O)N(R)-), ester (e.g., —OC(=O)— or —C(=O)O—), ether (e.g., —O—), ketone (e.g., —C(=O)—), thioether (e.g., —S—), sulfinyl (e.g., —S(O)—), sulfonyl (e.g., —S(O)$_2$—), or a direct (e.g., C—C bond) linkage, wherein each R is independently H or ($C_1$-$C_{14}$) alkyl. Such a linkage can be formed from suitably functionalized starting materials using synthetic procedures that are known in the art. Based on the linkage that is desired, one skilled in the art can select suitably functional starting materials that can be derived from a residue of a compound of formula I and from a given peptide residue or amino acid residue using procedures that are known in the art.

The peptide residue or amino acid residue can be directly linked to any synthetically feasible position on the residue of a compound of formula I. Suitable points of attachment include, for example, the b-carboxamide, the d-carboxamide, and the e-carboxamide (illustrated in FIG. 1), as well as the 6-position (the position occupied by X in FIG. 1)., and the 5'-hydroxy and the 3'-hydroxy groups on the 5-membered sugar ring, although other points of attachment are possible. U.S. Pat. No. 5,739,313 discloses compounds (e.g., cyanocobalamin-b-(4-aminobutyl)amide, methylcobalamin-b-(4-aminobutyl)amide, and adenosylcobalamin-b-(4-aminobutyl)amide) that are useful intermediates for the preparation of compounds of the present invention.

The invention also provides compounds having more than one peptide residue or amino acid residue attached to a compound of formula I. For example, the peptide residue or amino acid residue can be linked to a residue of the b-carboxamide of the compound of formula I and another peptide residue or amino acid residue can be directly linked to a residue of the d-carboxamide of the compound of formula I.

The residue of a compound of formula I can be prepared by any suitable means known in the art. For example, a monocarboxylic acid or dicarboxylic acid of cobalamin, wherein X is cyano, methyl, or adenosyl can be prepared as disclosed in U.S. Pat. No. 5,739,313. These compounds can be prepared by the mild acid hydrolysis of cyanocobalamin, which has been shown to yield a mixture of mono-, a dicarboxylic acid and one tricarboxylic acid. These carboxylic acids are derived from the propionamide side chains designated b, d and e, as discussed hereinabove, which are more susceptible to hydrolysis than the amide groups on acetamide side chains a, c, and g. The (b)-, (d)-, and (e)-monocarboxylic acids can be separated by column chromatography. See FIG. 1 hereinabove. L. Anton et al., J. Amer. Chem. Soc., 102, 2215 (1980). See, also, J. B. Armitage et al., J. Chem. Soc., 3349 (1953); K. Bemhauer, Biochem. Z., 344, 289 (1966); H. P. C. Hogenkamp et al., Biochemistry, 14, 3707 (1975); and L. Ellenbogen, in "Cobalamin," Biochem. and Pathophysiol., B. Babior, ed., Wiley, N.Y. (1975) at chapter 5.

Compounds wherein the peptide or amino acid is linked to the 6-position of the compound of formula I can be prepared by reducing a corresponding Co(II) compound of formula I to form a nucleophilic Co(I) compound, and treating the Co(I) compound with a suitable alkylating agent comprising an amino acid or peptide.

Particular values listed below for radicals, substituents, and ranges, are for illustration only and they do not exclude other defined values or other values within defined ranges for the radicals and substituents.

Specifically, the peptide can comprise 2 to about 20, about 5 to about 15, or about 6 to about 12 amino acids.

Specifically, the peptide can be about 5 to about 200 Angstroms, about 5 to about 150 Angstroms, about 5 to about 100 Angstroms, or about 5 to about 50 Angstroms.

Specifically, the peptide can be poly-L-lysine, comprising 2 to about 20 residues, about 5 to about 15 residues, or about 6 to about 12 residues.

Specifically, the peptide can be linked to more than one chelating group. More specifically, the peptide can be linked to 2 to about 10, 2 to about 8, 2 to about 6, or 2 to about 4 chelating groups.

Specifically, the peptide can comprise more than one non-metallic radioisotope. More specifically, the peptide can comprise 2 to about 10, 2 to about 8, 2 to about 6, or 2 to about 4 non-metallic radioisotopes.

Specifically, the amino acid can be Lys, His or Tyr.

Specifically, the amino acid can comprise more than one non-metallic radioisotope. More specifically, the amino acid can comprise 2 to about 4 non-metallic radioisotopes.

Suitable non-metallic radionuclides include Carbon-11, Fluorine-18, Bromine-76, Iodine-123, Iodine-124, and Iodine-131.

A specific peptide residue comprising one or more non-metallic radionuclides has the following formula

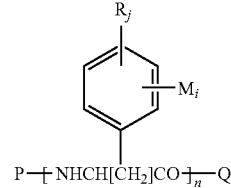

wherein each M is independently a suitable non-metallic radionuclide (e.g., Fluorine-18, Bromine-76, or Iodine-123); each R is independently ($C_1$-$C_{14}$) alkyl, ($C_2$-$C_{14}$)alkenyl, ($C_2$-$C_{14}$)alkynyl, ($C_1$-$C_{14}$)alkoxy, hydroxy, cyano, nitro, halo, trifluoromethyl, $N(R_a)(R_b)$, ($C_1$-$C_{14}$)alkanoyl, ($C_2$-$C_{14}$) alkanoyloxy, ($C_6$-$C_{10}$)aryl, or ($C_3$-$C_8$)cycloalkyl wherein $R_a$ and $R_b$ are each independently H or ($C_1$-$C_{14}$)alkyl; P is H, ($C_1$-$C_{14}$)alkyl, or a suitable amino protecting group; Q is H, ($C_1$-$C_{14}$)alkyl, or a suitable carboxy protecting group; n is 2 to about 20, about 5 to about 15, or about 6 to about 12; and wherein i is 1-5, j is 0-4 and i+j is≦5.

Specifically, i can be 1, j can be 0, M can be Fluorine-18, Bromine-76, Iodine-131, or Iodine-123, and n can be about 6 to about 12.

Specifically, the amino acid can be linked to more than one chelating group. More specifically, the amino acid can be linked to 2 to about 10, 2 to about 8, 2 to about 6, or 2 to about 4 chelating groups.

Specifically, a conjugate of a residue of vitamin $B_{12}$ and a residue of a peptide or an amino acid comprising a radionuclide can comprise more than one chelating group. More specifically, the cobalamin conjugate can comprise 2 to about 10, 2 to about 8, 2 to about 6, or 2 to about 4 chelating groups.

Specifically, a conjugate of a residue of vitamin $B_{12}$ and a residue of a peptide or an amino acid can comprise more than one radioisotope (i.e., radionuclide). More specifically, a conjugate of a residue of vitamin $B_{12}$ and a residue of a peptide or an amino acid can comprise 2 to about 10, 2 to about 8, 2 to about 6, or 2 to about 4 radioisotopes (i.e., radionuclides).

A "detectable chelating group" is a chelating group comprising a metallic radionuclide (e.g., a metallic radioisotope) capable of detecting cancer or other neoplastic cells in vivo or in vitro. Any suitable chelating group can be employed. Specifically, the chelating group can be NTA, HEDTA, DCTA, RP414, MDP, DOTATOC, CDTA, HYNIC, EDTA, DTPA, TETA, DOTA, DCTA, 15N4, 9N3, 12N3, or MAG3 (or another suitable polyamino acid chelator), which are described herein below, or a phosphonate chelator (e.g. EDMT). More specifically, the chelating group can be DTPA.

DTPA is diethylenetriaminepentaacetic acid; TETA is 1,4,8,11-tetraazacyclotetradecane-N,N',N'',N'''-tetraacetic acid; DOTA is 1,4,7,10-tetraazacyclododecane-N,N',N'',N'''-tetraacetic acid; 15N4 is 1,4,8,12-tetraazacyclopentadecane-N,N',N'',N'''-tetraacetic acid; 9N3 is 1,4,7-triazacyclononane-N,N',N''-triacetic acid; 12N3 is 1,5,9-triazacyclododecane-N,N',N''-triacetic acid; MAG3 is (N—[N—[N-[(benzoylthio) acetyl]glycyl]glycyl]glycine); and DCTA is a cyclohexane-based metal chelator of the formula

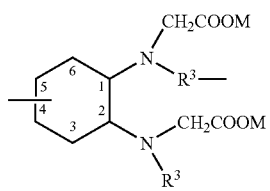

wherein $R^3$ may by $(C_1-C_{14})$alkyl or $CH_2CO_2$—, which may be attached through positions 4 or 5, or through the group $R^3$ and which carries from 1 to 4 detectable metal or nonmetal cations (M), monovalent cations, or the alkaline earth metals. Thus, with metals of oxidation state +1, each individual cyclohexane-based molecule may carry up to 4 metal cations (where both $R^3$ groups are $CH_2COOM$). As is more likely, with higher oxidation states, the number of metals will decrease to 2 or even 1 per cyclohexane skeleton. This formula is not intended to limit the molecule to any specific stereochemistry. NTA, HEDTA, and DCTA are disclosed in Poster Sessions, Proceedings of the 46th Annual Meeting, *J. Nuc. Med.*, p. 316, No. 1386. RP414 is disclosed in Scientific Papers, Proceedings of the 46th Annual Meeting, *J. Nuc. Med.*, p. 123, No. 499. MDP is disclosed in Scientific Papers, Proceedings of the 46th Annual Meeting, *J. Nuc. Med.*, p. 102, No. 413. DOTATOC is disclosed in Scientific Papers, Proceedings of the 46th Annual Meeting, *J. Nuc. Med.*, p. 102, No. 414 and Scientific Papers, Proceedings of the 46th Annual Meeting, *J. Nuc. Med.*, p. 103, No. 415. CDTA is disclosed in Poster Sessions, Proceedings of the 46th Annual Meeting, *J. Nuc. Med.*, p. 318, No. 1396. HYNIC is disclosed in Poster Sessions, Proceedings of the 46th Annual Meeting, *J. Nuc. Med.*, p. 319, No. 1398.

Bifunctional chelators based on macrocyclic ligands in which conjugation is via an activated arm attached to the carbon backbone of the ligand can also be employed as a chelating group, as described by M. Moi et al., *J. Amer. Chem. Soc.*, 49, 2639 (1989) (2-p-nitrobenzyl-1,4,7,10-tetraeacyclododecane-N,N',N'',N'''-tetraacetic acid); S. V. Deshpande et al., *J. Nucl. Med.*, 31, 473 (1990); G. Kuser et al., Bioconj. Chem., 1, 345 (1990); C. J. Broan et al., *J. C. S. Chem. Comm.*, 23, 1739 (1990); and C. J. Anderson et al., *J. Nucl. Med.*, 36, 850 (1995) (6-bromoacetamido-benzyl-1,4,8,11-tetraazacyclotetadecane-N,N',N'',N'''-tetraacetic acid (BAT)).

In addition, the diagnostic chelator or therapeutic chelator can be any of the chelators disclosed in Scientific Papers, Proceedings of the 46th Annual Meeting, *J. Nuc. Med.*, Wednesday, Jun. 9, 1999, p. 124, No. 500. A chelator may also include a molecule that contains two or more donor atoms capable of binding to a single metal ion. A chelator may include, for example, 1,4,7,10-tetraazacyclododecane N,N',N'''-triacetic acid (DO3A);, HP-DO3A; DTPA; DTPA-BMA; CHX-A" DTPA; 2-(rho-nitrobenzyl)-1,4,7,10-tetraazacyclododecane-N,N',N'',N'''-tetraacetic acid (nitro-DOTA); alpha-(2-(rho-nitrophenyl)ethyl)-1,4,7,10,-tetraazacyclododecane-1-acetic-4,7,10-tris(methylacetic) acid (nitro-PADOTA); 2-(rho-nitrobenzyl)-1,4,7,10-tetraazacyclotridecane-N,N',N'',N'''-tetraacetic acid (nitro-TRITA); N-[2-amino-3-(rho-nitrophenyl)propyl]-trans-cyclohexane-1,2-diamine-N,N',N''-pentaacetic acid (nitro-CHX-A-DTPA) and 2-methyl-6-(rho-nitrobenzyl)-1,4,7-triazaheptane-N,N,N',N'',N'''-pentaacetic acid (nitro-1B4M-DTPA or nitro-MX-DTPA); 6,6"-bis[[N,N,N'',N''-tetra(carboxymethyl)amino]methyl]-4'-(3-amino-4-methoxyphenyl)-2,2':6',2''-terpyridine (TMT-amine); 2-amiomethylpyridine; iminoacetic acid; iminodiacetic acid; 1-oxa-4,7,1triazacyclododecane-N,N'',N''-triacetic acid (OTTA); trans(1,2)-cyclohexanodiethylene-triamine-pentaacetic acid (CDTPA); DPDP; TMT; TETA 1,4,8,11-tetraazacyclotetradecane-N,N',N'',N'''-tetraacetic acid;

Additional examples include 2-p-nitrobenzyl-1,4,7,10-tetraazacyclododecane-N,N',N'',N'''-tetraacetic acid, carbonyliminodiacetic acid, methyleneiminoacetic acid, methyleneiminodiacetic acid, ethylenethioethyleneiminoacetic acid, ethylenethioethyleneiminodiacetic acid, a terpyridinyl group, a chelating agent comprising a terpyridyl group, a carboxymethylamino group, and combinations thereof. A chelator may include a salt, analog, homologue, or derivative of any of the chelators disclosed herein.

Suitable metallic radionuclides (i.e., metallic radioisotopes or metallic paramagnetic ions) include Actinium-225, Antimony-124, Antimony-125, Arsenic-74, Barium-139, Barium-140, Beryllium-7, Bismuth-206, Bismuth-207, Bismuth-212, Bismuth-213, Cadmium-109, Cadmium-115, Cadmium-15m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-67, Erbium-169, Europium-152, Gallium-64, Gallium-68, Gadolinium-153, Gadolinium-157 Gold-195, Gold-199, Hafnium-175, Hafnium-175-181, Holmium-166, Indium-110, Indium-111, Iridium-192, Iron-55, Iron-59, Krypton-85, Lead-210, Lead-212, Lutetium-177, Manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-147, Protactinium-233, Radium-223, Radium-226, Rhenium-186, Rhenium-188, Rubidium-86, Ruthenium-103, Ruthenium-106, Scandium-44, Scandium-46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-1 70, Tin-1 13, Tin-1 14, Tin-117m, Titanium-44, Tungsten-185, Vanadium-48, Vanadium-49, Ytterbium-169, Yttrium-86, Yttrium-88, Yttrium-90, Yttrium-91, Zinc-65, and Zirconium-95.

Specifically, the chelating group can comprise more than one metallic radioisotope. More specifically, the chelating group can comprise 2 to about 10, 2 to about 8, 2 to about 6, or 2 to about 4 metallic radioisotopes.

As used herein, a "detectable chelating group" is a chelating group comprising a metallic radionuclide (e.g., a metallic radioisotope) capable of detecting cancer or other neoplastic cells in a diagnostic procedure in vivo or in vitro. Any suitable chelating group can be employed. Specifically, the chelating group can be NTA, HEDTA, DCTA, RP414, MDP, DOTA-TOC, CDTA, HYNIC, EDTA, DTPA, TETA, DOTA, DOTMP, DCTA, 15N4, 9N3, 12N3, or MAG3. More specifically, the chelating group can be DTPA.

As used herein, a "detectable radionuclide" is any suitable radionuclide (i.e., radioisotope) capable of detecting cancer or other neoplastic cells in a diagnostic procedure in vivo or in vitro. Suitable detectable radionuclides include metallic radionuclides (i.e., metallic radioisotopes) and non-metallic radionuclides (i.e., non-metallic radioisotopes).

Specifically, the non-metallic radionuclide can be a non-metallic paramagnetic atom (e.g., Fluorine-19); a non-metallic positron emitting radionuclide (e.g., Carbon-11, Fluorine-18, Iodine-123, or Bromine-76); or a non-metallic gamma emitter (e.g., Iodine-131). Fluorine-18 is a suitable non-metallic radionuclide for use the compounds of the present invention in part because there is typically little or no background noise associated with the diagnostic use of fluorine in the body of a mammal (e.g., human).

Specifically, the metallic radionuclide can be a diagnostic gamma emitter (e.g., Tc-99m, In-111, or Iron-59); a diagnostic metallic positron emitting radionuclide (e.g., Bismuth-206, Bismuth-207, Cobalt-55, Gallium-64, Copper-67, Yttrium-86, or Yttrium-88); or a paramagnetic diagnosis metal ion (e.g., Europium-152 or Gadolinium-157).

As used herein, a "therapeutic radionuclide" is any suitable radionuclide (i.e., radioisotope) that possesses therapeutic efficacy against cancer or other neoplastic cells in vivo or in vitro. Suitable therapeutic radionuclides include metallic radionuclides (i.e., metallic radioisotopes).

Specifically, the metallic radionuclide can be a therapeutic metallic radionuclide (e.g., Actinium-223, Bismuth-212, Indium-111, Rhenium-186, Rhenium-188, Strontium-89, Tin-117m, and Yttrium-90) or a therapeutic paramagnetic metal ion (e.g., Gadolinium-157).

Specifically, the therapeutic radionuclide may be Iodine-131. For example, a protein (e.g., having tyrosine) or a chelator linked to cobalamin residue may comprise Iodine-131.

Specifically, the chelating group can be any one of the carbonyl complexes disclosed in Waibel et al., *Nature Biotechnology*, 897-901, Vol. 17, September 1999; or Sattelberger et al., *Nature Biotechnology*, 849-850, Vol. 17, September 1999.

Specifically, the chelating group can be any of the carbonyl complexes disclosed in Waibel et al., *Nature Biotechnology*, 897-901, Vol. 17, September 1999; or Sattelberger et al., *Nature Biotechnology*, 849-850, Vol. 17, September 1999, further comprising a metallic radionuclide. More specifically, the chelating group can be any of the carbonyl complexes disclosed in Waibel et al., *Nature Biotechnology*, 897-901, Vol. 17, September 1999; or Sattelberger et al., *Nature Biotechnology*, 849-850, Vol. 17, September 1999, further comprising Technetium-99m.

Specifically, the chelating group can be any of the carbonyl complexes disclosed in Waibel et al., *Nature Biotechnology*, 897-901, Vol. 17, September 1999; or Sattelberger et al., *Nature Biotechnology*, 849-850, Vol. 17, September 1999, further comprising a metallic radionuclide. More specifically, the chelating group can be any of the carbonyl complexes disclosed in Waibel et al., *Nature Biotechnology*, 897-901, Vol. 17, September 1999; or Sattelberger et al., *Nature Biotechnology*, 849-850, Vol. 17, September 1999.

Specifically, the chelating group can be DTPA and n can be 8 to 11.

The invention provides compounds wherein a residue of a compound of formula I is linked to a radionuclide. For such a compound, the radionuclide (e.g., detectable radionuclide) can be linked, directly or through a linker, to the residue of a compound of formula I.

A directly linked detectable radionuclide can be linked directly to any synthetically feasible position on the residue of a compound of formula I. Suitable points of attachment include, for example, the b-carboxamide, the d-carboxamide, and the e-carboxamide (illustrated in FIG. 1), as well as the 6-position (the position occupied by X in FIG. 1), and the 5'-hydroxy and the 3'-hydroxy groups on the 5-membered sugar ring, although other points of attachment are possible. U.S. Pat. No. 5,739,313 discloses compounds (e.g., cyanocobalamin-b-(4-aminobutyl)amide, methylcobalamin-b-(4-aminobutyl)amide, and adenosylcobalamin-b-(4-aminobutyl)amide) that are useful intermediates for the preparation of compounds of the present invention.

When a radionuclide is linked to the residue of a compound of formula I by a suitable linker, the structure of the linker is not crucial, provided it provides a compound of the invention which has an effective therapeutic and/or diagnostic index against the target cells, and which will localize in or near tumor molecules.

Suitable linkers include linkers that separate the residue of a compound of formula I and the detectable radionuclide by about 5 angstroms to about 200 angstroms, inclusive, in length. Other suitable linkers include linkers that separate the residue of a compound of formula I and the detectable radionuclide by about 5 angstroms to about 100 angstroms, as well as linkers that separate the residue of a compound of formula I and the detectable radionuclide by about 5 angstroms to about 50 angstroms, or by about 5 angstroms to about 25 angstroms. Suitable linkers are disclosed, for example, in U.S. Pat. No. 5,739,313.

Specifically, the linker can be a divalent radical of the formula W-A wherein A is $(C_1-C_6)$alkyl, $(C_2-C_6)$alkenyl, $(C_2-C_6)$alkynyl, $(C_3-C_8)$cycloalkyl, or $(C_6-C_{10})$aryl, wherein W is —N(R)C(=O)—, —C(=O)N(R)—, —OC(=O)—, —C(=O)O—, —O—, —S—, —S(O)—, —S(O)$_2$—, —N(R)-, —C(=O)—, or a direct bond; wherein each R is independently H or $(C_1-C_6)$alkyl; wherein A is linked to one or more non-metallic radionuclides.

The compounds disclosed herein can be prepared using procedures similar to those described in U.S. Pat. No. 5,739,313, or using procedures similar to those described herein. Additional intermediates and synthetic preparations useful for preparing compounds of the present invention are disclosed, for example, in Hogenkamp, H. et al., *Synthesis and Characterization of nido-Carborane-Cobalamin Conjugates*, Nucl. Med. & Biol., 2000, 27, 89-92; Collins, D., et al., *Tumor Imaging Via Indium 111-Labeled DTPA-Adenosylcobalamin*, Mayo Clinic Proc., 1999, 74:687-691; U.S. Application Ser. No. 60/129,733 filed 16 Apr. 1999; U.S. Application Ser. No. 60/159,874 filed 15 Oct. 1999; U.S. Application Ser. No. 60/159,753 filed 15 Oct. 1999; U.S. Application Ser. No. 60/159,873 filed 15 Oct. 1999; and references cited therein.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The present invention provides a method of imaging a tumor in a mammal. The tumor can be located in any part of the mammal. Specifically, the tumor can be located in the breast, lung, thyroid, lymph node, genitourinary system (e.g., kidney, ureter, bladder, ovary, teste, or prostate), musculoskeletal system (e.g., bones, skeletal muscle, or bone marrow), gastrointestinal tract (e.g., stomach, esophagus, small bowel, colon, rectum, pancreas, liver, or smooth muscle), central or peripheral nervous system (e.g., brain, spinal cord, or nerves), head and neck tumors (e.g., ears, eyes, nasopharynx, oropharynx, or salivary glands), liver, spleen, kidney, pancreas, salivary glands, parathyroid, vessels (e.g., arteries, veins, capillaries), adrenals, gall bladder, or the heart. The tumor can be located in a soft tissue location (e.g., Enzinger and Weiss's Soft Tissue Tumors, Mosby, 2001).

The compound of the present invention (cobalamin conjugates) can be formulated as pharmaceutical compositions and administered to a mammalian host, such as a human patient in a variety of forms adapted to the chosen route of administration, i.e., by intravenous, intramuscular, or subcutaneous routes.

The cobalamin conjugates can be administered intravenously or intraperitoneally by infusion or injection. Solutions of the substance can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions comprising the substance which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, normal saline, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the substance in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Depending on the diagnostic radionuclide utilized to label the cobalamin peptide conjugates, the suitable dose ranges between 500 µCi to 20 mCi. This is based on both human and swine biodistribution studies (D A Collins, H P C Hogenkamp, M W Gebard, Tumor Imaging Indium-111-labeled DTPA-adenosylcobalamin, Mayo Clinic Proceedings, 1999; 74; 687-691; Biodistribution of Radiolabeled Adenosylcobalamin in Humans, Review of 30 patents submitted to Mayo Clinic Proceedings).

The invention will now be illustrated by the following non-limiting Examples.

EXAMPLES

Poly-L-lysine hydrobromide (MW 500-2000) and (MW 1000-4000), adenosine, 1-ethyl-3(3'-dimethylaminopropyl) carbodiimide, trifluoroacetic acid, trifluoroacetic anhydride, 2,2,2-trifluoroethylamine hydrochloride and 1-hydroxybenzotriazole were purchased from Sigma Chemical Co. Sephodex-G-10 was purchased from Pharmacia Biotech, Inc. Thin layer chromatography (TLC) silica gel plates were obtained from Eastman Kodak Co. Solvents and other reagents were obtained in the highest purity available. Cyanocobalamin-b, d and e monocarboxylic acid and the b,d-dicarboxylic acid were prepared as described before (Anton, D. L., Hogenkamp, H. P. C., Walker, T. E. and Matwiyoff, N. A., Carbon-13 nuclear magnetic resonance studies of the monocarboxylic acids of cyanocobalamin. Assignments of the b-, d-, and e-monocarboxylic acids, *J. Am. Chem. Soc.*, 102, 2215-2219 (1980)). 5'chloro-5'-deoxyadenosine was synthesized by the method of Kikugawa and Ichino (Kikugawa, K. and Ichino, M., *Tetrahedron Lett.*, 87 (1971)). The adenosylcobalamin-monocarboxylic acid was prepared as described before (Hogenkamp, H. P. C., Chemical synthesis and properties of analogs of adenosylcobalamin, *Biochemistry*, 13, 2736-2740 (1974)).

Example 1

Cyanocobalamin-Poly L-Lysine-DTPA Conjugate. Poly-L-lysine hydrobromide (Sigma no. PO879), degree of polymerization~11 units, molecular weight range 1000-4000 (500 mg) was dissolved in water (20 ml). Cyanocobalamin-b-monocarboxylic acid (150 mg, ~100 µmol), 1-ethyl-3(3'-dimethylaminopropyl) carbodiimide (480 mg, 2.5 mmol) and hydroxybenzotriazole (338 mg, 2.5 mmol) were added. The pH of the mixture was adjusted and maintained at approximately 8 with 1 N sodium hydroxide. The progress of the reaction was monitored by thin layer chromatography on silica gel sheets using isopropanol-ammonium hydroxide-water (7:1:2) as the developing agent.

Upon completion of the reaction, the mixture was applied to a column of Sephadex G-10 (3×40 cm). The column was eluted with water and 2 ml fractions were collected. The red eluents that reacted with ninhydrin were pooled and freeze dried (i.e., lyophilized).

Recovery of the cyanocobalamin-poly-L-lysine complex (about 70%) was obtained. The cyanocobalamin-poly-L-lysine complex was dissolved in water (10 ml) and a saturated solution of sodium bicarbonate (10 ml) and DTPA bisanhydride (Sigma) (375 mg, 1 mmol) were added.

The progress of the reaction was monitored by TLC as described above. The cyanocobalamin-poly-L-lysine-DTPA conjugate was purified on Sephadex G-10 as described above. The final product was freeze dried and isolated as a red powder.

Example 2

Cyanocobalamin-Poly L-Lysine-DTPA Conjugate. Poly-L-lysine (Sigma no. 8954) degree of polymerization ~8 units, molecular weight range 500-2000 (500 mg) was dissolved in water (20 ml). Cyanocobalamin-b-monocarboxylic acid (150 mg, ~100 µmols), 1-ethyl-3(3'-dimethylaminopropyl) carbodiimide (480 mg, 2.5 mmol) and hydroxybenzotriazole (338 mg, 2.5 mmol) were added. The pH of the mixture was adjusted and maintained at approximately 8 with 1 N sodium hydroxide. The progress of the reaction was monitored by thin layer chromatography on silica gel sheets using isopropanol-ammonium hydroxide-water (7:1:2) as the developing agent.

Upon completion of the reaction, the mixture was applied to a column of Sephadex G-10 (3×40 cm). The column was eluted with water and 2 ml fractions were collected. The red eluents that reacted with ninhydrin were pooled and freeze dried (i.e., lyophilized).

Recovery of the cyanocobalamin-poly-L-lysine complex (about 70%) was obtained. The cyanocobalamin-poly-L-lysine complex was dissolved in water (10 ml) and a saturated solution of sodium bicarbonate (10 ml) and DTPA bisanhydride (Sigma) (375 mg, 1 mmol) were added.

The progress of the reaction was monitored by TLC as described above. The cyanocobalamin-poly-L-lysine-DTPA conjugate was purified on Sephadex G-10 as described above. The final product was freeze dried and isolated as a red powder.

Example 3

Imaging Data. In vitro unsaturated $B_{12}$ binding capacity (UBBC) has demonstrated that cyanocobalamin-poly-L-lysine, cyanocobalamin-poly-L-lysine-polyDTPA compounds have in vitro biological activity that is 92% and 43.4% when compared to cyanocobalamin. Comparison of cyanocobalamin-DTPA to cyanocobalamin was 66.4% (Transcobalamin II receptor imaging via radiolabeled diethylene-triaminepentaacetate cobalamin analogs, J. Nucl. Med., 38, 717-723 (1997); also described in U.S. Pat. No. 5,739,313). The specific activity has been increased from 300 µCi in the cobalamin mono-DTPA compounds to 4.5 mCi with the cobalamin poly-L-lysine-polyDTPA complex (D A Collins, H P C Hogenkamp, M W Gebard, Tumor Imaging Indium-111-labeled DTPA-adenosylcobalamin, Mayo Clinic Proceedings, 1999; 74; 687-691; Biodistribution of Radiolabeled Adenosylcobalamin in Humans, Review of 30 patents submitted to Mayo Clinic Proceedings). This should improve tumor-to-background ratio, which can be evaluated in murine tumor models. Attachment of either the adenosyl and methyl group as the beta ligand should improve the biological activity as it did with the cyanocobalamin mono-DTPA compound (Transcobalamin II receptor imaging via radiolabeled diethylene-triaminepentaacetate cobalamin analogs, J. Nucl. Med., 38, 717-723 (1997); also described in U.S. Pat. No. 5,739,313).

Example 4

Synthesis of Adenosyltrifluoroethylamidocobalamins

Figure 3:
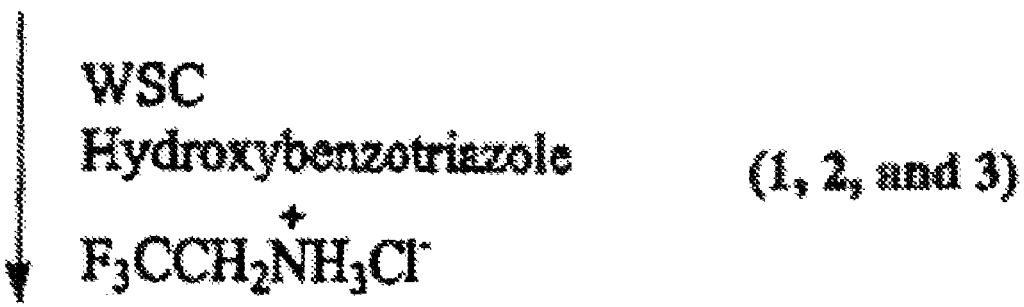
FIG. 3 illustrates a synthesis of representative compounds of the invention (8, 9) wherein a residue of a compound of formula I is linked to a non-metallic radionuclide (e.g., Fluorine-18 or Iodine-131).
Figure 3:
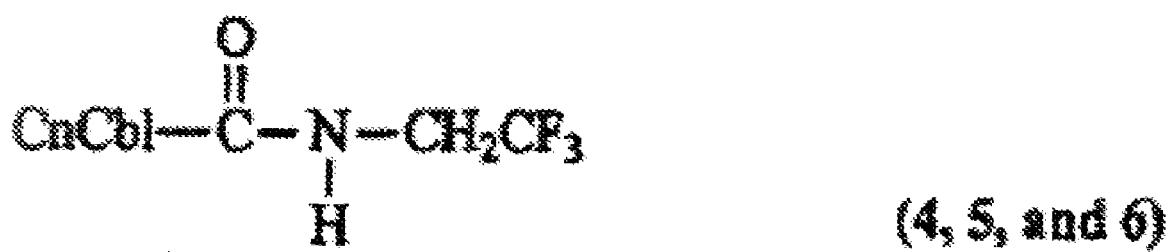
Figure 3:
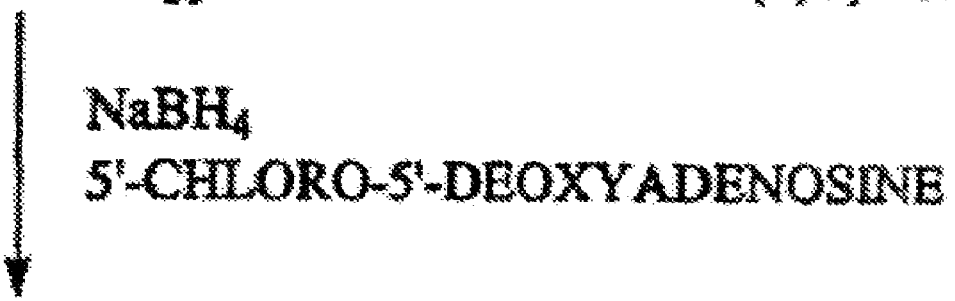
Figure 3:

Adenosyltrifluoroethylamidocobalamins (compounds 8 and 9, FIG. 3). Separately the b- and e-cyanotrifluoroethylamidocobalamins (compounds 5, 6) 500 mg (~0.33 mmol) were reduced with sodium borohydride to their cobalt (I) forms, which in turn were reacted with 5'chloro-5'-deoxyadenosine as described before (Hogenkamp, H. P. C., Chemical synthesis and properties of analogs of adenosylcobalamin, Biochemistry, 13, 2736-2740 (1974)). The reaction mixtures were acidified to pH 3 with 1N HCl and applied to separate columns of A6 50×2 (200-400 mesh, pH 3.0). The columns were washed with water and the desired adenosylcobalamins eluted with 0. 1 M sodium acetate pH 6A. After desalting by extraction into phenol as described above, both 8 and 9 were isolated as red powders. Yields 315 mg and 320 mg respectively.

The intermediates, compounds 4, 5, and 6, were prepared as follows:

(A.) Cyanotrifluoroethylamidocobalamins (compounds 4, 5, and 6, FIG. 3). Separate reaction mixtures containing 600 mg (~0.4 mmol) of the b, d and e-cyanocobalamin monocarboxylic acids (compounds 1, 2, 3, FIG. 3), hydroxybenzotriazole 540 mg (4 mmol), 1-ethyl-3(3'-dimethylaminopropyl) carbodiimide 768 mg (4 mmol) and 2,2,2-trifluoroethylamino hydrochloride 678 mg (5 mmol) were dissolved in 50 mL water and the pH adjusted to 6.8 with 1N NaOH. The progress of the reactions was monitored by TLC using 2-propanol-$NH_4OH$-water (7:1:2) as the solvent. After 2 hr incubation at room temperature, the mixtures were extracted into 92% aqueous phenol. The phenol layers were extensively washed with water to remove the water-soluble reagents. One volume of acetone and three volumes of ether were then added to the phenol phases and the desired fluorocobalamins were back extracted into water. The aqueous phases were extracted three times with ether to remove residual phenol. The solutions were concentrated on a rotary evaporator and the fluorocobalamins crystallized from aqueous acetone. Yields 4,600 mg; 5,540 mg; 6,470 mg.

Example 5

Figure 5:
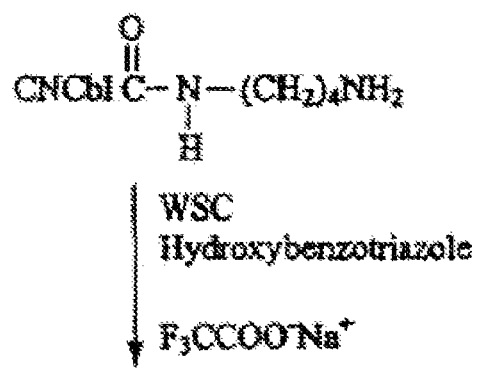
FIG. 5 illustrates a synthesis of a compound of the present invention (10) wherein a residue of a compound of formula I is linked to a non-metallic radionuclide (e.g., Fluorine-18 or Iodine-131) through a linker.
Figure 5:
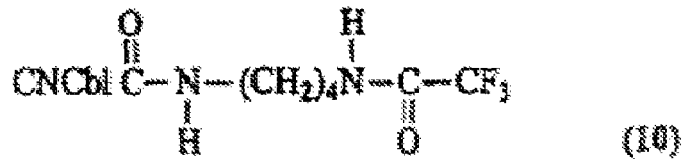

Cyano-b-trifluoroacetamido butylamide cobalamin (compound 10, FIG. 5). Cyanocobalamin-b-(9-aminobutyl) amide (600 mg, ~0.4 mmol) was prepared as described by Collins, D. A. and Hogenkamp, H. P. C., Transcobalamin II receptor imaging via radiolabeled diethylenetriaminepentaacetate cobalamin analogs, J. Nucl. Med., 38, 717-723 (1997), hydroxybenzotriazole 540 mg (4 mmol), 1-ethyl-3(3'-dimethylaminopropyl) carbodiimide 768 mg (4 mmol) and sodium trifluoroacetate (680 mg, 5 mmol) were dissolved in 50 mL water and the pH adjusted to 6.2 with 1N NaOH. After incubation at room temperature for 5 hr, the reaction mixture was desalted as described above. The resulting aqueous solution was purified by column chromatography (A6, 50×2, 200-400 mesh, pH 3.0) and the pass through collected. The solution was concentrated and compound 10 was crystallized from aqueous acetone. Yield 315 mg.

Example 6

Figure 4:
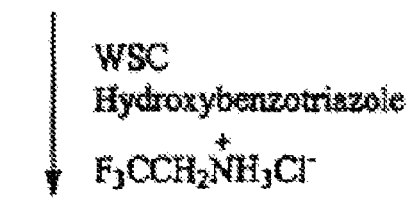
FIG. 4 illustrates a synthesis of a compound of the present invention (7) wherein a residue of a compound of formula I is linked to a non-metallic radionuclide (e.g., Fluorine-18 or Iodine-131) through a linker.

Cyano-bis-trifluoroethylamidocobalamin (compound 7, FIG. 4). A reaction mixture containing cyanocobalamin-b,d-dicarboxylic acid (540 mg, ~0.36 mmol) was reacted with 2,2,2-trifluoroethylamine hydrochloride 678 mg (5 mmol) as described above, compound 7 was crystallized from aqueous acetone. Yield 630 mg.

Example 7

Figure 6:
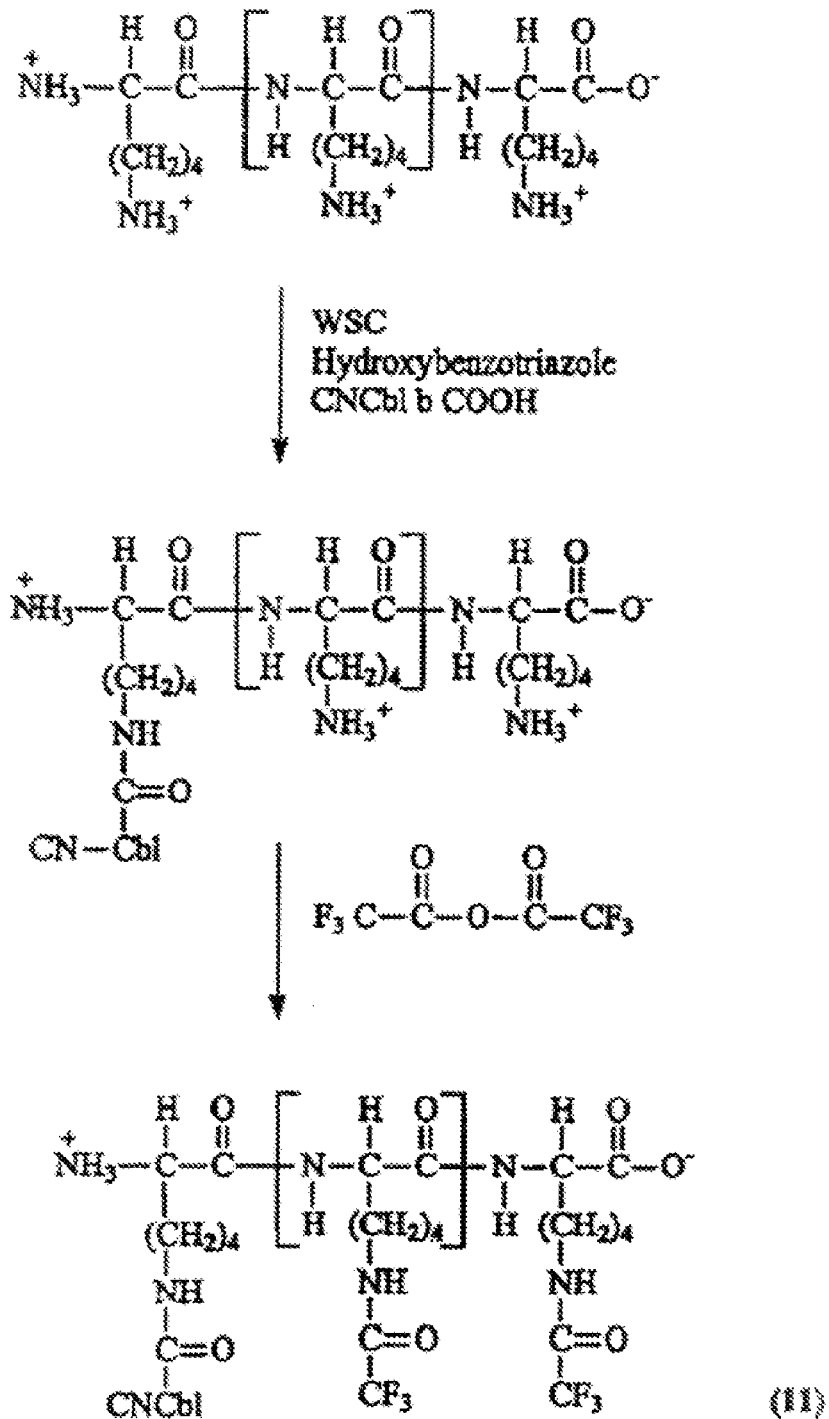
FIG. 6 illustrates a synthesis of a compound of the present invention (11) wherein a residue of a compound of formula I is linked to a peptide residue that comprises a non-metallic radionuclide (e.g., Fluorine-18 or Iodine-131).

Cyanotrifluoroacetyl polylysine cobalamin (compound 11, FIG. 6). Poly-L-lysine hydrobromide (MW 500-2000) 500 mg, cyanocobalamin-b-carboxylic acid 300 mg (~0.2 mmol), hydroxybenzotriazole (338 mg, 2.5 mmol) and 1-ethyl-3(3'-dimethylaminopropyl) carbodiimide 480 mg (2.5 mmol) were dissolved in 10 mL of water and the pH adjusted to 6.5 with 1N NaOH. After incubation at room temperature for 4 hr, the reaction mixture was purified by chromatography (Sephodex G-10, 40×3 cm), which was eluted with water. The red eluents, that also reacted with ninhydrin, were pooled and freeze dried. The freeze-dried preparation was dissolved in 10 mL saturated sodium bicarbonate and reacted with 1 mL of trifluoroacetic anhydride for 1 hr. The preparation was again purified by chromatography and lyophilized to yield 490 mg of compound 11 as a fluffy powder.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound wherein a residue of a compound of formula I

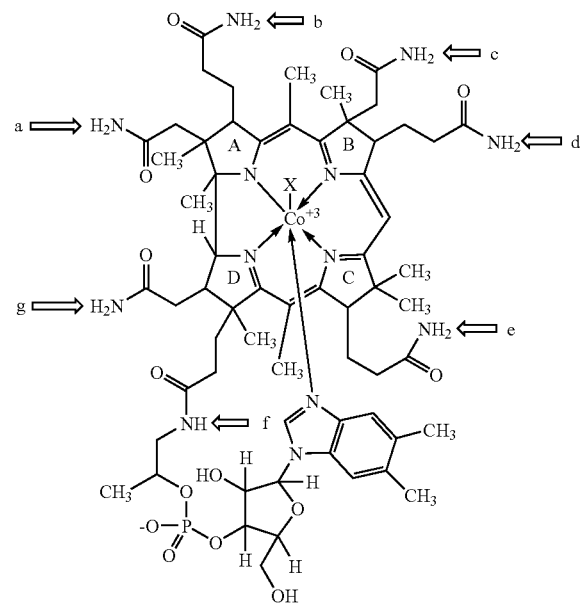

is linked to one or more peptide residues or amino acid residues wherein X is CN, OH, $CH_3$ or adenosyl, and at least one of the peptide residues or the amino acid residues is linked to one or more chelating groups comprising one or more metallic radionuclides independently selected from the group consisting of Actinium-225, Barium-139, Bismuth-212, Bismuth-213, Cadmium-115, Lead-212, Lutetium-177, and Radium-223; or a pharmaceutically acceptable salt thereof.

2. The compound of claim 1 wherein the residue of a compound of formula I is linked to a peptide residue at the position of the b-carboxamide, d-carboxamide, e-carboxamide, or the 6-position of the compound of formula I.

3. The compound of claim 1 wherein the residue of a compound of formula I is linked to a peptide residue at the position of the b-carboxamide of the compound of formula I.

4. The compound of claim 1 wherein the residue of a compound of formula I is linked to a peptide residue at the d-carboxamide of the compound of formula I.

5. The compound of claim 1 wherein the residue of a compound of formula I is linked to a peptide residue or an amino acid residue at the e-carboxamide of the compound of formula I.

6. The compound of claim 1 wherein the residue of a compound of formula I is linked to a peptide residue or an amino acid residue at the 6-position of the compound of formula I.

7. The compound of claim 1 wherein at least one peptide residue comprises 2 to about 20 amino acids.

8. The compound of claim 7 wherein at least one peptide residue is a residue of poly-L-lysine.

9. The compound of claim 1 wherein at least one peptide residue is linked to more than one chelating group.

10. The compound of claim 1 wherein at least one peptide residue is linked to 2 to about 4 chelating groups.

11. The compound of claim 1 wherein at least one chelating group is EDTA, DTPA, DTPA-BMA, MX-DTPA, CHX-A"DTPA, CDTPA, TETA, DOTA, DOTMP, DCTA, MAG3, DO3A, TMT, or OTTA.

12. The compound of claim 1 wherein at least one chelating group is DTPA.

13. The compound of claim 1 wherein a residue of a compound of formula I is linked to a residue of formula —[NHCH[$(CH_2)_4NH_2$-DET]CO-]$_n$-Q wherein Q is H, ($C_1$-$C_{14}$)alkyl, or a suitable carboxy protecting group; and DET is a chelating group residue comprising a metallic radionuclide and wherein n is between 2 and about 20.

14. The compound of claim 13 wherein the chelating group is DTPA.

15. The compound of claim 1 wherein the residue of a compound of formula I is linked to two peptide residues wherein at least one peptide residue is linked to one or more chelating groups comprising one or more metallic radionuclides.

16. A compound wherein a residue of a compound of formula I

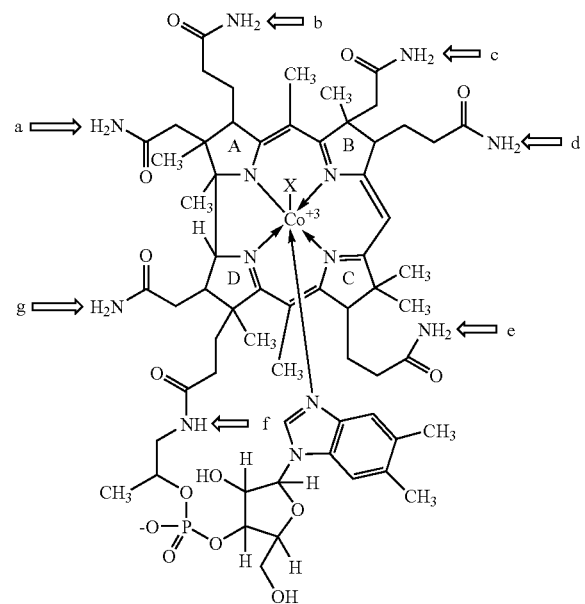

is linked to one or more residues of the formula —[NHCH[(CH$_2$)$_4$NH$_2$-DET]CO-]$_n$-Q wherein Q is H, (C$_1$-C$_{14}$)alkyl, or a suitable carboxy protecting group; X is CN, OH, CH$_3$ or adenosyl; DET is a chelating group residue comprising a metallic radionuclide selected from the group consisting of Actinium-225, Barium-139, Bismuth-212, Bismuth-213, Cadmium-115, Lead-212, Lutetium-177, and Radium-223; and n is between 2 and about 20; or a pharmaceutically acceptable salt thereof.

17. The compound of claim 16 wherein the chelating group is DTPA.

18. The compound of claim 16 wherein n is about 8 to about 11.

19. The compound of claim 16 wherein the residue of a compound of formula I is linked to two residues of the formula P-[NHCH[(CH$_2$)$_4$NH$_2$-DET]CO-]$_n$-Q wherein P is H, (C$_1$-C$_{14}$)alkyl, or a suitable amino protecting group; Q is H, (C$_1$-C$_{14}$)alkyl, or a suitable carboxy protecting group; and DET is independently a chelating group residue comprising a metallic radionuclide and wherein n is 2 to about 20.

20. The compound of claim 1 wherein the residue of a compound of formula I is further linked to one or more detectable radionuclides.

21. The compound of claim 20 wherein the detectable radionuclide is a non-metallic radionuclide.

22. The compound of claim 21 wherein the non-metallic radionuclide is Carbon-11, Fluorine-18, Bromine-76, Iodine-123, or Iodine-124.

23. The compound of claim 20 wherein the detectable radionuclide is directly linked to the compound of formula I.

24. The compound of claim 20 wherein the detectable radionuclide is linked by a linker to the compound of formula I.

25. The compound of claim 24 wherein the linker is of the formula W-A wherein A is (C$_1$-C$_6$)alkyl, (C$_2$-C$_6$)alkenyl, (C$_2$-C$_6$)alkynyl, (C$_3$-C$_8$)cyclo-alkyl, or (C$_6$-C$_{10}$)aryl, wherein W is —N(R)C(=O)—, —C(=O)N(R)-, —OC(=O)—, —C(=O)O—, —O—, —S—, —S(O)—, —S(O)$_2$—, —N(R)-, —C(=O), or a direct bond; wherein each R is independently H or (C$_1$-C$_6$)alkyl; and wherein A is linked to one or more non-metallic radionuclides.

26. The compound of claim 24 wherein the linker is about 5 angstroms to about 50 angstroms, inclusive, in length.

27. The compound of claim 24 wherein the linker is linked to the 6-position of the compound of formula I or is linked to the residue of a-, b-, d- or e-carboxamide group of the compound of formula I.

28. A compound wherein a residue of a compound of formula I

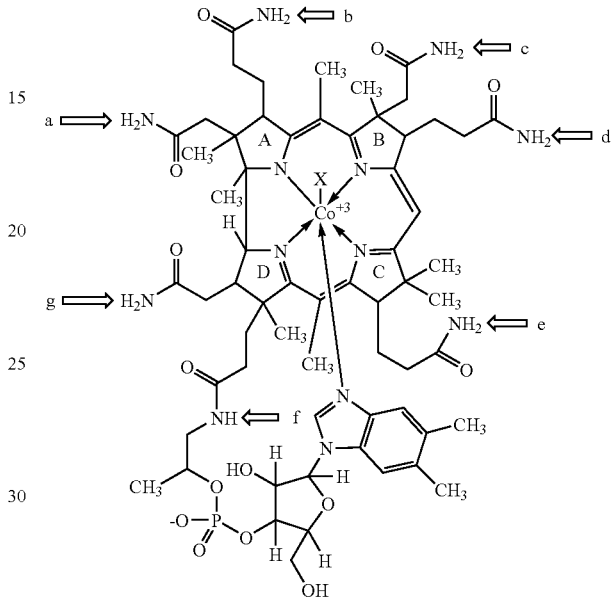

is linked to a residue of a peptide which is linked to one or more chelating groups comprising a metallic radionuclide selected from the group consisting of Actinium-225, Barium-139, Bismuth-212, Bismuth-213, Cadmium-115, Lead-212, Lutetium-177, and Radium-223; and X is CN, OH, CH$_3$ or adenosyl; or a pharmaceutically acceptable salt thereof.

29. A compound wherein a residue of a compound of formula I

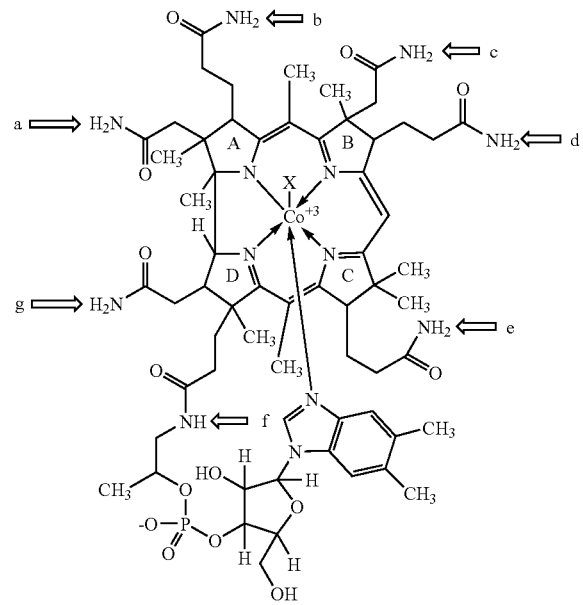

is linked to a residue of an amino acid which is linked to one or more chelating groups comprising a metallic radionuclide selected from the group consisting of Actinium-225, Barium-139, Bismuth-212, Bismuth-213, Cadmium-115, Lead-212, Lutetium-177, and Radium-223; and X is CN, OH, $CH_3$ or adenosyl; or a pharmaceutically acceptable salt thereof.

30. A pharmaceutical composition comprising a compound of any one of claims 1, 2, 3, 4, 5, 6, 7, 8, 9, 10, 11, 12, 13, 14, 15, 16, 17, 18, 19, 20, 21, 22, 23, 24, 25, 26, 27, 28, or 29, and a pharmaceutically acceptable carrier.

31. A method for imaging a tumor in mammalian tissue comprising administering to the mammal an amount of a compound of any one of claims 1, 2, 3, 4, 5, 6, 7, 8, 9, 10, 11, 12, 13, 14, 15, 16, 17, 18, 19, 20, 21, 22, 23, 24, 25, 26, 27, 28, or 29 and detecting said compound.

32. The method of claim 31 wherein the mammal is a human.

33. The method of claim 31 wherein the mammalian tissue is located in a breast, lung, thyroid, lymph node, genitourinary system, musculoskeletal system, gastrointestinal tract, central or peripheral nervous system, head, neck, liver, spleen, kidney, pancreas, salivary glands, parathyroid, vessel, adrenals, gall bladder, heart, or a soft tissue.

34. A method for treating a tumor in a mammal comprising administering to the mammal an effective therapeutic amount of a compound of any one of claims 1, 2, 3, 4, 5, 6, 7, 8, 9, 10, 11, 12, 13, 14, 15, 16, 17, 18, 19, 20, 21, 22, 23, 24, 25, 26, 27, 28, or 29; wherein said compound comprises at lease one therapeutic radionuclide.

35. The method of claim 34 wherein the mammal is a human.

36. The method of claim 34 wherein the mammalian tissue is located in a breast, lung, thyroid, lymph node, genitourinary system, musculoskeletal system, gastrointestinal tract, central or peripheral nervous system, head, neck, liver, spleen, kidney, pancreas, salivary glands, parathyroid, vessel, adrenals, gall bladder, heart, or a soft tissue.

37. A compound of anyone of claims 1, 2, 3, 4, 5, 6, 7, 8, 9, 10, 11, 12, 13, 14, 15, 16, 17, 18, 19, 20, 21, 22, 23, 24, 25, 26, 27, 28, or 29 for use in medical therapy or diagnosis.

38. A compound wherein a residue of a compound of formula I

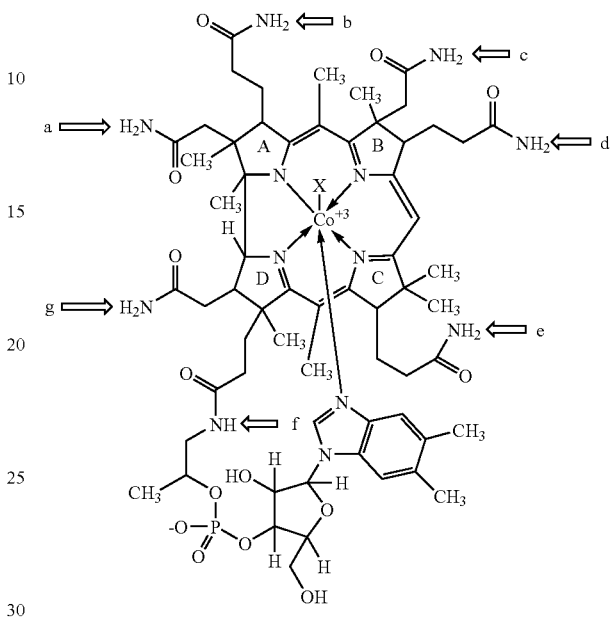

is linked to one or more peptide residues or amino acid residues wherein X is CN, OH, $CH_3$ or adenosyl, and at least one of the peptide residues or the amino acid residues is linked to Iodine-131 or a pharmaceutically acceptable salt thereof.

* * * * *

UNITED STATES PATENT AND TRADEMARK OFFICE
CERTIFICATE OF CORRECTION

PATENT NO.        : 7,591,995 B2                                    Page 1 of 1
APPLICATION NO.   : 11/555034
DATED             : September 22, 2009
INVENTOR(S)       : Douglas A. Collins It is certified that error appears in the above-identified patent and that said Letters Patent is hereby corrected as shown below:

Column 18, line 47 (Claim 11), please delete "A "DTPA" and insert --A" DTPA-- therefor;

Column 18, line 54 (Claim 13), please delete "$[(CH_2)_4NH_2\text{-DET}]CO\text{-}]_n\text{-}Q$" and insert --$[(CH_2)_4NH_2\text{—DET}]CO\text{—}]_n\text{—}Q$-- therefor;

Column 19, line 30 (Claim 16), please delete "$[(CH_2)_4NH_2\text{-DET}]CO\text{-}]_n\text{-}Q$" and insert --$[(CH_2)_4NH_2\text{—DET}]CO\text{—}]_n\text{—}Q$-- therefor;

Column 19, line 44 (Claim 19), please delete "$P\text{-}[NHCH[(CH_2)_4NH_2\text{-DET}]CO\text{-}]_n\text{-}Q$" and insert --$P\text{—}[NHCH[(CH_2)_4NH_2\text{—DET}]CO\text{—}]_n\text{—}Q$-- therefor;

Column 19, line 65 (Claim 25), please delete "—N(R)C(=O) —,—C(=O)N(R)-" and insert -- —N(R)C(=O) —,—C(=O)N(R)— -- therefor;

Column 19, line 67 (claim 25), please delete "—N(R)-, —C(=O)" and insert -- —N(R) —,—C(=O)-- therefor;

Column 21, claim 28 (Claim 34), please delete "at lease" and insert --at least-- therefor.

Signed and Sealed this

Twenty-second Day of December, 2009

David J. Kappos
*Director of the United States Patent and Trademark Office*